(12) United States Patent
Pierce et al.

(10) Patent No.: US 11,504,418 B2
(45) Date of Patent: Nov. 22, 2022

(54) ENDOTOXIN FREE ASPARAGINASE

(71) Applicant: CROWPIERCE TECHNOLOGIES, LLC, Canton, GA (US)

(72) Inventors: George E. Pierce, Canton, GA (US); Sidney A. Crow, Smyrna, GA (US)

(73) Assignee: CROWPIERCE TECHNOLOGIES, LLC, Canton, GA (US)

( * ) Notice: Subject to any disclaimer, the term of this patent is extended or adjusted under 35 U.S.C. 154(b) by 287 days.

(21) Appl. No.: 16/347,427

(22) PCT Filed: Nov. 2, 2017

(86) PCT No.: PCT/US2017/059655
§ 371 (c)(1),
(2) Date: May 3, 2019

(87) PCT Pub. No.: WO2018/085493
PCT Pub. Date: May 11, 2018

(65) Prior Publication Data
US 2019/0275121 A1 Sep. 12, 2019

Related U.S. Application Data

(60) Provisional application No. 62/417,456, filed on Nov. 4, 2016.

(51) Int. Cl.
*A61K 38/50* (2006.01)
*A61K 47/60* (2017.01)
*C12P 13/20* (2006.01)
*C12N 9/82* (2006.01)

(52) U.S. Cl.
CPC .............. *A61K 38/50* (2013.01); *A61K 47/60* (2017.08); *C12N 9/82* (2013.01); *C12P 13/20* (2013.01); *C12Y 305/01001* (2013.01)

(58) Field of Classification Search
None
See application file for complete search history.

(56) References Cited

U.S. PATENT DOCUMENTS

| | | | |
|---|---|---|---|
| 5,731,176 A | 3/1998 | Yamada et al. | |
| 6,251,388 B1 | 6/2001 | Durden | |
| 7,531,343 B2 | 5/2009 | Pierce et al. | |
| 2004/0209345 A1 | 10/2004 | Nagasawa et al. | |
| 2016/0060613 A1* | 3/2016 | Abribat | A61K 47/60 424/94.6 |

FOREIGN PATENT DOCUMENTS

| | | |
|---|---|---|
| WO | 0059533 A1 | 10/2000 |
| WO | 2007090122 A2 | 8/2007 |

OTHER PUBLICATIONS

Jinta et al., J. Med. Dent. Sci. 62:1-9, 2015 (Year: 2015).*
McDermott et al., Bioorg. Med. Chem. 24:1819-1839, 2016 (Year: 2016).*
Thai et al., Nat. Comm. 6:8873, 2015, 9 pages (Year: 2015).*
Singh et al., Curr. Protein Pept. Sci. 18:1-11, 2017 (Year: 2017).*
Zhang et al.,Structure 26:1474-1485, 2018 (Year: 2018).*
El-Naggar et al., Purification, characterization, cytotoxicity and anticancer activities of L-asparaginase, anti-colon cancer protein, from the newly isolated alkaliphilic Streptomyces fradiae NEAE-82, Scientific Reports, vol. 6, No. 32926, p. 1-16, 2016.
International Search Report issued for PCT/US17/59655, dated Mar. 5, 2018.
Komeda, H., et al: "A Novel Gene Cluster Including the Rhodococcus Rhodochrous J1 MHLBA Genes Encoding a Low Molecular Mass Nitrile Hydratase (L-NHase) Induced by Its Reaction Product", Journal of Biological Chemistry, American Society for Biochemistry and Molecular Biology, US, vol. 271, No. 26, Jun. 28, 1996.
Komeda Hidenobu et al: "Characterization of the gene cluster of highmolecular-mass nitrile hydratase (H-NHase) induced by its reaction product in Rhodococcus rhodochrous J1 ", Proceedings of the National Academy of Sciences, National Academy of Sciences, US, vol. 93, No. 9, Apr. 1, 1996.
Extended European Search Report issued in corresponding European application No. 17867001.4, dated Mar. 16, 2020; 7 pages.

* cited by examiner

*Primary Examiner* — David Steadman
(74) *Attorney, Agent, or Firm* — Meunier Carlin & Curfman LLC

(57) ABSTRACT

Disclosed herein is an endotoxin-free asparaginase enzyme. Also disclosed are methods of using the disclosed enzyme to treat subjects with a disease treatable by depletion of asparagine. For example, the disclosed endotoxin-free asparaginase enzyme is useful in the treatment or the manufacture of a medicament for use in the treatment of acute lymphoblastic leukemia (ALL) in both adults and children, as well as other conditions where asparagine depletion is expected to have a useful effect.

7 Claims, 5 Drawing Sheets
Specification includes a Sequence Listing.

FIG. 2

SEQUENCE LISTING

```
<160> NUMBER OF SEQ ID NOS: 24

<210> SEQ ID NO 1
<211> LENGTH: 624
<212> TYPE: DNA
<213> ORGANISM: Rhodococcus rhodochrous

<400> SEQUENCE: 1
atgaccgccc ataatcccgt ccagggcacg ttgccacgat cgaacgagga gatcgccgca      60
cgcgtgaagg ccatggaggc catcctcgtc gacaagggcc tgatctccac cgacgccatc     120
gaccacatgt cctcggtcta cgagaacgag gtcggtcctc aactcggcgc caagatcgtc     180
gcccgcgcct gggtcgatcc cgagttcaag cagcgcctgc tcaccgacgc caccggcgcc     240
tgccgtgaaa tgggcgtcgg cggcatgcag ggcgaagaaa tggtcgtgct ggaaaacacc     300
```

-continued

```
gacacggtcc acaacatggt cgtatgtacc ttgtgctcgt gctatccgtg gccggttctc    360
ggcctgccac ccaactggta caagtacccc gcctaccgcg cccgcgctgt ccgcgacccc    420
cgaggtgtgc tggccgaatt cggatatacc cccgaccctg acgtcgagat ccggatatgg    480
gactcgagtg ccgaacttcg ctactgggtc ctgccgcaac gcccaaccgg caccgagaac    540
ttcaccgaag aacaactcgc cgacctcgtc acccgcgact cgctcatcgg cgtatccgtc    600
cccaccacac ctagcaaggc ctga                                           624
```

```
<210> SEQ ID NO 2
<211> LENGTH: 207
<212> TYPE: PRT
<213> ORGANISM: Rhodococcus rhodochrous

<400> SEQUENCE: 2
```

```
Met Thr Ala His Asn Pro Val Gln Gly Thr Leu Pro Arg Ser Asn Glu
1               5                   10                  15

Glu Ile Ala Ala Arg Val Lys Ala Met Glu Ala Ile Leu Val Asp Lys
            20                  25                  30

Gly Leu Ile Ser Thr Asp Ala Ile Asp His Met Ser Ser Val Tyr Glu
        35                  40                  45

Asn Glu Val Gly Pro Gln Leu Gly Ala Lys Ile Val Ala Arg Ala Trp
    50                  55                  60

Val Asp Pro Glu Phe Lys Gln Arg Leu Leu Thr Asp Ala Thr Gly Ala
65                  70                  75                  80

Cys Arg Glu Met Gly Val Gly Gly Met Gln Gly Glu Glu Met Val Val
                85                  90                  95

Leu Glu Asn Thr Asp Thr Val His Asn Met Val Val Cys Thr Leu Cys
            100                 105                 110

Ser Cys Tyr Pro Trp Pro Val Leu Gly Leu Pro Pro Asn Trp Tyr Lys
        115                 120                 125

Tyr Pro Ala Tyr Arg Ala Arg Ala Val Arg Asp Pro Arg Gly Val Leu
    130                 135                 140

Ala Glu Phe Gly Tyr Thr Pro Asp Pro Asp Val Glu Ile Arg Ile Trp
145                 150                 155                 160

Asp Ser Ser Ala Glu Leu Arg Tyr Trp Val Leu Pro Gln Arg Pro Thr
                165                 170                 175

Gly Thr Glu Asn Phe Thr Glu Glu Gln Leu Ala Asp Leu Val Thr Arg
            180                 185                 190

Asp Ser Leu Ile Gly Val Ser Val Pro Thr Thr Pro Ser Lys Ala
        195                 200                 205
```

```
<210> SEQ ID NO 3
<211> LENGTH: 681
<212> TYPE: DNA
<213> ORGANISM: Rhodococcus rhodochrous

<400> SEQUENCE: 3
```

```
atggatggaa tccacgacct cggtggccgc gccggcctgg gtccgatcaa gcccgaatcc     60
gatgaacctg ttttccattc cgattgggag cggtcggttt tgacgatgtt cccggcgatg    120
gccctggccg gcgcgttcaa tctcgaccag ttcggggcg cgatggagca gatcccccccg    180 cacgactacc tgacctcgca atactacgag cactggatgc acgcgatgat ccaccacggc    240
atcgaggcgg gcatcttcga ttccgacgaa ctcgaccgcc gcacccagta ctacatggac    300
catccggacg aaacgacccc cacgcggcag gatccgcaac tggtggagac gatctcgcaa    360
```

| | |
|---|---|
| ctgatcaccc acggagccga ttaccgacgc ccgaccgaca ccgaggccgc attcgccgta | 420 |
| ggcgacaaag tcatcgtgcg gtcggacgcc tcaccgaaca cccacacccg ccgcgccggg | 480 |
| tacgtccgcg gtcgtgtcgg cgaagtcgtg gcgacccacg gcgcgtatgt ctttccggac | 540 |
| accaacgcac tcggcgccgg cgaaagcccc gaacacctgt acaccgtgcg gttctcggcg | 600 |
| accgagttgt ggggtgaacc tgccgccccg aacgtcgtca atcacatcga cgtgttcgaa | 660 |
| ccgtatctgc taccggcctg a | 681 |

<210> SEQ ID NO 4
<211> LENGTH: 226
<212> TYPE: PRT
<213> ORGANISM: Rhodococcus rhodochrous

<400> SEQUENCE: 4

Met Asp Gly Ile His Asp Leu Gly Gly Arg Ala Gly Leu Gly Pro Ile
1               5                   10                  15

Lys Pro Glu Ser Asp Glu Pro Val Phe His Ser Asp Trp Glu Arg Ser
            20                  25                  30

Val Leu Thr Met Phe Pro Ala Met Ala Leu Ala Gly Ala Phe Asn Leu
        35                  40                  45

Asp Gln Phe Arg Gly Ala Met Glu Gln Ile Pro Pro His Asp Tyr Leu
    50                  55                  60

Thr Ser Gln Tyr Tyr Glu His Trp Met His Ala Met Ile His His Gly
65                  70                  75                  80

Ile Glu Ala Gly Ile Phe Asp Ser Asp Glu Leu Asp Arg Arg Thr Gln
                85                  90                  95

Tyr Tyr Met Asp His Pro Asp Glu Thr Thr Pro Thr Arg Gln Asp Pro
            100                 105                 110

Gln Leu Val Glu Thr Ile Ser Gln Leu Ile Thr His Gly Ala Asp Tyr
        115                 120                 125

Arg Arg Pro Thr Asp Thr Glu Ala Ala Phe Ala Val Gly Asp Lys Val
    130                 135                 140

Ile Val Arg Ser Asp Ala Ser Pro Asn Thr His Thr Arg Arg Ala Gly
145                 150                 155                 160

Tyr Val Arg Gly Arg Val Gly Glu Val Val Ala Thr His Gly Ala Tyr
                165                 170                 175

Val Phe Pro Asp Thr Asn Ala Leu Gly Ala Gly Glu Ser Pro Glu His
            180                 185                 190

Leu Tyr Thr Val Arg Phe Ser Ala Thr Glu Leu Trp Gly Glu Pro Ala
        195                 200                 205

Ala Pro Asn Val Val Asn His Ile Asp Val Phe Glu Pro Tyr Leu Leu
    210                 215                 220

Pro Ala
225

<210> SEQ ID NO 5
<211> LENGTH: 612
<212> TYPE: DNA
<213> ORGANISM: Rhodococcus rhodochrous

<400> SEQUENCE: 5

| | |
|---|---|
| gtgagcgagc acgtcaataa gtacacggag tacgaggcac gtaccaaggc aatcgaaacc | 60 |
| ttgctgtacg agcgagggct catcacgccc gccgcggtcg accgagtcgt ttcgtactac | 120 |
| gagaacgaga tcggcccgat gggcggtgcc aaggtcgtgg ccaagtcctg ggtggaccct | 180 |

-continued

```
gagtaccgca agtggctcga agaagacgcg acggccgcga tggcgtcatt gggctatgcc      240
ggcgagcagg cacaccagat ctcggccgtc ttcaacgact cccaaacaca tcacgtagtg      300
gtgtgcactc tgtgttcgtg ctatccgtgg ccggtgcttg gcctcccgcc cgcctggtac      360
aagagcatgg agtaccggtc ccgagtggta gcagaccctc gtggagtact caagcgcgat      420
ttcgggttcg acatccccga tgaggtggag gtcagggttt gggacagcag ctccgaaatc      480
cgctacatcg tcatcccgga acggccggcc ggcaccgacg gttggtccga ggacgagctg      540
gcgaagctgg tgagtcggga ctcgatgatc ggtgtcagta atgcgctcac accgcaggaa      600
gtgatcgtat ga                                                         612
```

<210> SEQ ID NO 6
<211> LENGTH: 203
<212> TYPE: PRT
<213> ORGANISM: Rhodococcus rhodochrous

<400> SEQUENCE: 6

```
Val Ser Glu His Val Asn Lys Tyr Thr Glu Tyr Glu Ala Arg Thr Lys
 1               5                  10                  15

Ala Ile Glu Thr Leu Leu Tyr Glu Arg Gly Leu Ile Thr Pro Ala Ala
                20                  25                  30

Val Asp Arg Val Val Ser Tyr Tyr Glu Asn Glu Ile Gly Pro Met Gly
            35                  40                  45

Gly Ala Lys Val Val Ala Lys Ser Trp Val Asp Pro Glu Tyr Arg Lys
        50                  55                  60

Trp Leu Glu Glu Asp Ala Thr Ala Ala Met Ala Ser Leu Gly Tyr Ala
 65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
        195                 200
```

<210> SEQ ID NO 7
<211> LENGTH: 690
<212> TYPE: DNA
<213> ORGANISM: Rhodococcus rhodochrous

<400> SEQUENCE: 7

```
atggatggta tccacgacac aggcggcatg accggatacg accggtcccc ctatcagaag       60
gacgagccct tcttccacta cgagtgggag ggtcgaaccc tgtcgattct gacctggatg      120
catctcaagg gcatgtcgtg gtgggacaag tcgcggttct tccggagtc gatggggaac      180 gaaaactacg tcaacgagat tcgcaactcg tactacaccc actggctgag tgcggcggaa      240
```

-continued

```
cgtatcctcg tcgccgacaa gatcatcacc gaagaagagc gaaagcaccg cgtgcaggag      300
atcctcgagg gtcggtacac ggacaggaac ccgtcgcgga agttcgatcc ggccgagatc      360
gagaaggcga tcgagaggct tcacgagccc cactccctag tgcttccagg agcggagccg      420
agtttctccc tcggtgacaa ggtcaaagtg aagaacatga acccgctggg acacacacgg      480
tgcccgaagt atgtgcggaa cagaatcggg gaaatcgtca cctcccacgg gtgccagatc      540
tatcccgaga gcagctccgc cggcctcggc gacgatcccc gcccgctcta cacggtcgcg      600 tttccgccc aggaactgtg gggcgacgac ggaaacggga agacgtagt gtgcgtcgat       660 ctctgggaac cgtacctgat ctctgcgtga                                      690
```

<210> SEQ ID NO 8
<211> LENGTH: 229
<212> TYPE: PRT
<213> ORGANISM: Rhodococcus rhodochrous

<400> SEQUENCE: 8

```
Met Asp Gly Ile His Asp Thr Gly Gly Met Thr Gly Tyr Gly Pro Val
 1               5                  10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Met Ser Trp Trp
            35                  40                  45

Asp Lys Ser Arg Phe Phe Arg Glu Ser Met Gly Asn Glu Asn Tyr Val
        50                  55                  60

Asn Glu Ile Arg Asn Ser Tyr Tyr Thr His Trp Leu Ser Ala Ala Glu
 65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Asn Pro Ser
                100                 105                 110

Arg Lys Phe Asp Pro Ala Glu Ile Glu Lys Ala Ile Glu Arg Leu His
            115                 120                 125

Glu Pro His Ser Leu Val Leu Pro Gly Ala Glu Pro Ser Phe Ser Leu
        130                 135                 140

Gly Asp Lys Val Lys Val Lys Asn Met Asn Pro Leu Gly His Thr Arg
145                 150                 155                 160

Cys Pro Lys Tyr Val Arg Asn Arg Ile Gly Glu Ile Val Thr Ser His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
210                 215                 220

Tyr Leu Ile Ser Ala
225
```

<210> SEQ ID NO 9
<211> LENGTH: 975
<212> TYPE: DNA
<213> ORGANISM: Rhodococcus rhodochrous

<400> SEQUENCE: 9

```
ttgagcgtcg aactcgtgga agtggtgcga tcggggttcc gcgaatgcgt gcaccgcggc      60
```

```
tcgctcgtcg tactcgaccc ggccggcgac gtgcggctcg cactgggcga gatccgcacg    120
ccgatctatc cgcggtcgtc gaacaagccg ctgcaggcgg tggcgctgct cggcagggc     180 ttcgtgcccc gctcgacgga ggaactcgcg atcgcgacgg cctcgcacga gggcgaggcc    240
gggcacgtcc ggctggtgga ggcgctgctc gccgggcacg gattcaccga ggacgacctg    300
cagtgcccgc cggatctgcc gggcaacgaa ccggcccggg cgacgatcgt cgccgccggt    360 caccccggc ggacggtgta catgaactgc tccggcaagc acgccgcgat gctcgcgacg     420
tgcgccgcga acggctggcc cgtccgcgcc ggcgcggacg agccgggcta cctcgactcc    480
gcccatccgc tgcagcaggc cgtggtcgag acggtcctcg acctcgcggg cgacgtcgag    540
gacaccgatc tcggcatcga cgggtgcggc ctgccgatcg tgccgctgcc cctggtcaat    600
ctcgcccggg cctattcgcg gctggcgacg gccgggcccg gacgccgga acgggccgtg     660 gccgacgcga tccggagtca tccgcacctc gtctcgggca ccggcaagga cgacgcccgg    720
ttgatgcccg cggtgccggg actgctgtgc aaggccgggg cggacggcgt gcacgcgggt    780
gccctgccgg acggcaccgc gttcgcactg aagatcgacg acgccacga gcgggcccgc     840 cttcccctca ctgccgccct gctgcaccac ctcggagtga cgtggtccga ggagcacgcg    900
gagctcgcgt cgcagccggt gctcggcggt gggatccggg tcggcacggt ccgggcgatc    960
cccggagtgc tctga                                                    975
```

<210> SEQ ID NO 10
<211> LENGTH: 324
<212> TYPE: PRT
<213> ORGANISM: Rhodococcus rhodochrous

<400> SEQUENCE: 10

```
Leu Ser Val Glu Leu Val Glu Val Arg Ser Gly Phe Arg Glu Cys
 1               5                  10                  15

Val His Arg Gly Ser Leu Val Val Leu Asp Pro Ala Gly Asp Val Arg
                 20                  25                  30

Leu Ala Leu Gly Glu Ile Arg Thr Pro Ile Tyr Pro Arg Ser Ser Asn
             35                  40                  45

Lys Pro Leu Gln Ala Val Ala Leu Leu Arg Gln Gly Phe Val Pro Arg
     50                  55                  60

Ser Thr Glu Glu Leu Ala Ile Ala Thr Ala Ser His Glu Gly Glu Ala
 65                  70                  75                  80

Gly His Val Arg Leu Val Glu Ala Leu Leu Ala Gly His Gly Phe Thr
                 85                  90                  95

Glu Asp Asp Leu Gln Cys Pro Pro Asp Leu Pro Gly Asn Glu Pro Ala
            100                 105                 110

Arg Ala Thr Ile Val Ala Ala Gly His Pro Arg Arg Thr Val Tyr Met
        115                 120                 125

Asn Cys Ser Gly Lys His Ala Ala Met Leu Ala Thr Cys Ala Ala Asn
    130                 135                 140

Gly Trp Pro Val Arg Ala Gly Ala Asp Glu Pro Gly Tyr Leu Asp Ser
145                 150                 155                 160

Ala His Pro Leu Gln Gln Ala Val Val Glu Thr Val Leu Asp Leu Ala
                165                 170                 175

Gly Asp Val Glu Asp Thr Asp Leu Gly Ile Asp Gly Cys Gly Leu Pro
            180                 185                 190

Ile Val Pro Leu Pro Leu Val Asn Leu Ala Arg Ala Tyr Ser Arg Leu
        195                 200                 205
```

```
Ala Thr Ala Gly Pro Gly Thr Pro Glu Arg Ala Val Ala Asp Ala Ile
    210                 215                 220

Arg Ser His Pro His Leu Val Ser Gly Thr Gly Lys Asp Asp Ala Arg
225                 230                 235                 240

Leu Met Pro Ala Val Pro Gly Leu Leu Cys Lys Ala Gly Ala Asp Gly
                245                 250                 255

Val His Ala Gly Ala Leu Pro Asp Gly Thr Ala Phe Ala Leu Lys Ile
                260                 265                 270

Asp Asp Gly His Glu Arg Ala Arg Leu Pro Leu Thr Ala Ala Leu Leu
            275                 280                 285

His His Leu Gly Val Thr Trp Ser Glu Glu His Ala Glu Leu Ala Ser
    290                 295                 300

Gln Pro Val Leu Gly Gly Ile Arg Val Gly Thr Val Arg Ala Ile
305                 310                 315                 320

Pro Gly Val Leu

<210> SEQ ID NO 11
<211> LENGTH: 1548
<212> TYPE: DNA
<213> ORGANISM: Rhodococcus rhodochrous

<400> SEQUENCE: 11
atgtcttcgt tgactccccc caattccaac caaatgtcgg ccctgaacaa ccacttccga      60
ttcggactga cgacgccgga actcgaagag ttcgcaccgg ccctcgaagc gacgctcgcg     120
tcctccgaaa ccgtcgaacg cctctacgag cgcaccgcgc ccgagccgcc tcagcggtca     180
tggacctcac ccacggcgga cgagaacccg ctgagcgcct ggtacgtcac cacctcgatc     240
agcgaaaccg acgaaggccc cctcgccggg cgaacggtcg ccgtgaaaga caacgtcgca     300
gtcgccggcg tgccgatgat gaacggctcc cgaaccgtcg agggcttcac ccccgctac      360 gacgccaccg tcgtacgccg actgctcgac gccggcgcaa ccatcaccgg caaagcggtg     420
tgcgaagatc tctgcttctc cggcgccagc ttcacttccc accccagcc ggtccgcaac      480 ccctgggacg aaagccgcat caccggcggc tcgtccagcg gcagcggcgc cctggtcgcc     540
agcggccagg tggatatggc agtcggcggc gaccaggggc gttcgatccg catccccgcc     600
gcgttctgcg catcgtcgg acacaaaccc acccacggac tggtcccta cgggagca        660 tttcccatcg aacgaaccat cgaccacctc ggtccgatga cgcgcaccgt cagcgacgcc     720
gccgcaatgc tcaccgtcct cgccggcacc gacggcctcg atccccgaca gacccaccgg     780
atcgaaccgg tggactacct cgcggcgctg gccgaaccg catcgggtct cgcgtgggt      840 gtggtcaccg aaggcttcga cacccctgtc tccgacgctg ccgtcgacaa tgccgtgcgc     900
accgccatcg gcgtactgcg ctcggccgga cttaccgtcg aagaggtctc gatcccctgg     960
cacctcgatg cgatggccgt ctggaacgtg atcgccaccg agggagcggc ctaccagatg    1020
ctcgacggca tgcctacgg catgaacact gatggcttct acgatcccga actgatcgcc     1080
cacttctccc gtcaacgact cgagcacggt caccaactgt cgaagacggt caaactcgtc    1140
gggatgtccg gcgcctacac attggaggta ggcggcggca agtactacgc catggcccgc    1200
caactcgtcc ccgaagtccg cgccgcctac gacgccgcct ggctcggta cgacgtgctg     1260 gtgatgccca cctccccta caccgccacc aagatcccga ccacggacat tccgttggcc     1320
gactatctgg acaccgcact gtcgatgatc atcaacaccg caccattcga cgtcaccggt    1380 cacccccgcct gcagtgtccc cgctgacctg gtccacgggc ttcccaccgg aatgatgatc    1440
```

```
atcggcaagc atttcgacga cgcgacagtg ctgcgcgtcg cccagctcta cgaacatgca    1500
gtgggcaact atcctgtccc gccggctgca gccggcaccc tgacataa                 1548
```

<210> SEQ ID NO 12
<211> LENGTH: 515
<212> TYPE: PRT
<213> ORGANISM: Rhodococcus rhodochrous

<400> SEQUENCE: 12

```
Met Ser Ser Leu Thr Pro Pro Asn Ser Asn Gln Met Ser Ala Leu Asn
1               5                   10                  15

Asn His Phe Arg Phe Gly Leu Thr Thr Pro Glu Leu Glu Glu Phe Ala
            20                  25                  30

Pro Ala Leu Glu Ala Thr Leu Ala Ser Ser Glu Thr Val Glu Arg Leu
        35                  40                  45

Tyr Glu Arg Thr Ala Pro Glu Pro Pro Gln Arg Ser Trp Thr Ser Pro
    50                  55                  60

Thr Ala Asp Glu Asn Pro Leu Ser Ala Trp Tyr Val Thr Thr Ser Ile
65                  70                  75                  80

Ser Glu Thr Asp Glu Gly Pro Leu Ala Gly Arg Thr Val Ala Val Lys
                85                  90                  95

Asp Asn Val Ala Val Ala Gly Val Pro Met Met Asn Gly Ser Arg Thr
            100                 105                 110

Val Glu Gly Phe Thr Pro Arg Tyr Asp Ala Thr Val Val Arg Arg Leu
        115                 120                 125

Leu Asp Ala Gly Ala Thr Ile Thr Gly Lys Ala Val Cys Glu Asp Leu
    130                 135                 140

Cys Phe Ser Gly Ala Ser Phe Thr Ser His Pro Gln Pro Val Arg Asn
145                 150                 155                 160

Pro Trp Asp Glu Ser Arg Ile Thr Gly Gly Ser Ser Gly Ser Gly
                165                 170                 175

Ala Leu Val Ala Ser Gly Gln Val Asp Met Ala Val Gly Gly Asp Gln
            180                 185                 190

Gly Gly Ser Ile Arg Ile Pro Ala Ala Phe Cys Gly Ile Val Gly His
        195                 200                 205

Lys Pro Thr His Gly Leu Val Pro Tyr Thr Gly Ala Phe Pro Ile Glu
    210                 215                 220

Arg Thr Ile Asp His Leu Gly Pro Met Thr Arg Thr Val Ser Asp Ala
225                 230                 235                 240

Ala Ala Met Leu Thr Val Leu Ala Gly Thr Asp Gly Leu Asp Pro Arg
                245                 250                 255

Gln Thr His Arg Ile Glu Pro Val Asp Tyr Leu Ala Ala Leu Ala Glu
            260                 265                 270

Pro Ala Ser Gly Leu Arg Val Gly Val Val Thr Glu Gly Phe Asp Thr
        275                 280                 285

Pro Val Ser Asp Ala Ala Val Asp Asn Ala Val Arg Thr Ala Ile Gly
    290                 295                 300

Val Leu Arg Ser Ala Gly Leu Thr Val Glu Glu Val Ser Ile Pro Trp
305                 310                 315                 320

His Leu Asp Ala Met Ala Val Trp Asn Val Ile Ala Thr Glu Gly Ala
                325                 330                 335

Ala Tyr Gln Met Glu Asp Gly Asn Ala Tyr Gly Met Asn Thr Asp Gly
            340                 345                 350

Phe Tyr Asp Pro Glu Leu Ile Ala His Phe Ser Arg Gln Arg Leu Glu
```

```
                355                 360                 365
        His Gly His Gln Leu Ser Lys Thr Val Lys Leu Val Gly Met Ser Gly
            370                 375                 380

Arg Tyr Thr Leu Glu Val Gly Gly Lys Tyr Tyr Ala Met Ala Arg
        385                 390                 395                 400

Gln Leu Val Pro Glu Val Arg Ala Ala Tyr Asp Ala Ala Leu Ala Arg
                        405                 410                 415

Tyr Asp Val Leu Val Met Pro Thr Leu Pro Tyr Thr Ala Thr Lys Ile
                    420                 425                 430

Pro Thr Thr Asp Ile Pro Leu Ala Asp Tyr Leu Asp Thr Ala Leu Ser
                435                 440                 445

Met Ile Ile Asn Thr Ala Pro Phe Asp Val Thr Gly His Pro Ala Cys
                450                 455                 460

Ser Val Pro Ala Asp Leu Val His Gly Leu Pro Thr Gly Met Met Ile
        465                 470                 475                 480

Ile Gly Lys His Phe Asp Asp Ala Thr Val Leu Arg Val Ala Gln Leu
                        485                 490                 495

Tyr Glu His Ala Val Gly Asn Tyr Pro Val Pro Pro Ala Ala Ala Gly
                    500                 505                 510

Thr Leu Thr
                515

<210> SEQ ID NO 13
<211> LENGTH: 433
<212> TYPE: PRT
<213> ORGANISM: Rhodococcus rhodochrous

<400> SEQUENCE: 13

Met Thr Ala His Asn Pro Val Gln Gly Thr Leu Pro Arg Ser Asn Glu
        1               5                   10                  15

Glu Ile Ala Ala Arg Val Lys Ala Met Glu Ala Ile Leu Val Asp Lys
                    20                  25                  30

Gly Leu Ile Ser Thr Asp Ala Ile Asp His Met Ser Ser Val Tyr Glu
                35                  40                  45

Asn Glu Val Gly Pro Gln Leu Gly Ala Lys Ile Val Ala Arg Ala Trp
            50                  55                  60

Val Asp Pro Glu Phe Lys Gln Arg Leu Leu Thr Asp Ala Thr Gly Ala
        65                  70                  75                  80

Cys Arg Glu Met Gly Val Gly Gly Met Gln Gly Glu Glu Met Val Val
                        85                  90                  95

Leu Glu Asn Thr Asp Thr Val His Asn Met Val Val Cys Thr Leu Cys
                    100                 105                 110

Ser Cys Tyr Pro Trp Pro Val Leu Gly Leu Pro Pro Asn Trp Tyr Lys
                115                 120                 125

Tyr Pro Ala Tyr Arg Ala Arg Ala Val Arg Asp Pro Arg Gly Val Leu
            130                 135                 140

Ala Glu Phe Gly Tyr Thr Pro Asp Pro Asp Val Glu Ile Arg Ile Trp
        145                 150                 155                 160

Asp Ser Ser Ala Glu Leu Arg Tyr Trp Val Leu Pro Gln Arg Pro Thr
                        165                 170                 175

Gly Thr Glu Asn Phe Thr Glu Glu Gln Leu Ala Asp Leu Val Thr Arg
                    180                 185                 190

Asp Ser Leu Ile Gly Val Ser Val Pro Thr Thr Pro Ser Lys Ala Met
                195                 200                 205
```

```
Asp Gly Ile His Asp Leu Gly Gly Arg Ala Gly Leu Gly Pro Ile Lys
    210                 215                 220

Pro Glu Ser Asp Glu Pro Val Phe His Ser Asp Trp Glu Arg Ser Val
225                 230                 235                 240

Leu Thr Met Phe Pro Ala Met Ala Leu Ala Gly Ala Phe Asn Leu Asp
                245                 250                 255

Gln Phe Arg Gly Ala Met Glu Gln Ile Pro Pro His Asp Tyr Leu Thr
            260                 265                 270

Ser Gln Tyr Tyr Glu His Trp Met His Ala Met Ile His His Gly Ile
        275                 280                 285

Glu Ala Gly Ile Phe Asp Ser Asp Glu Leu Asp Arg Arg Thr Gln Tyr
    290                 295                 300

Tyr Met Asp His Pro Asp Glu Thr Thr Pro Thr Arg Gln Asp Pro Gln
305                 310                 315                 320

Leu Val Glu Thr Ile Ser Gln Leu Ile Thr His Gly Ala Asp Tyr Arg
                325                 330                 335

Arg Pro Thr Asp Thr Glu Ala Ala Phe Ala Val Gly Asp Lys Val Ile
            340                 345                 350

Val Arg Ser Asp Ala Ser Pro Asn Thr His Thr Arg Arg Ala Gly Tyr
        355                 360                 365

Val Arg Gly Arg Val Gly Glu Val Val Ala Thr His Gly Ala Tyr Val
    370                 375                 380

Phe Pro Asp Thr Asn Ala Leu Gly Ala Gly Glu Ser Pro Glu His Leu
385                 390                 395                 400

Tyr Thr Val Arg Phe Ser Ala Thr Glu Leu Trp Gly Glu Pro Ala Ala
                405                 410                 415

Pro Asn Val Val Asn His Ile Asp Val Phe Glu Pro Tyr Leu Leu Pro
            420                 425                 430

Ala

<210> SEQ ID NO 14
<211> LENGTH: 432
<212> TYPE: PRT
<213> ORGANISM: Rhodococcus rhodochrous

<400> SEQUENCE: 14

Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140
```

-continued

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val Met Asp Gly Ile His
        195                 200                 205

Asp Thr Gly Gly Met Thr Gly Tyr Gly Pro Val Pro Tyr Gln Lys Asp
210                 215                 220

Glu Pro Phe Phe His Tyr Glu Trp Gly Arg Thr Leu Ser Ile Leu
225                 230                 235                 240

Thr Trp Met His Leu Lys Gly Met Ser Trp Trp Asp Lys Ser Arg Phe
                245                 250                 255

Phe Arg Glu Ser Met Gly Asn Glu Asn Tyr Val Asn Glu Ile Arg Asn
            260                 265                 270

Ser Tyr Tyr Thr His Trp Leu Ser Ala Ala Glu Arg Ile Leu Val Ala
        275                 280                 285

Asp Lys Ile Ile Thr Glu Glu Arg Lys His Arg Val Gln Glu Ile
290                 295                 300

Leu Glu Gly Arg Tyr Thr Asp Arg Asn Pro Ser Arg Lys Phe Asp Pro
305                 310                 315                 320

Ala Glu Ile Glu Lys Ala Ile Glu Arg Leu His Glu Pro His Ser Leu
                325                 330                 335

Val Leu Pro Gly Ala Glu Pro Ser Phe Ser Leu Gly Asp Lys Val Lys
            340                 345                 350

Val Lys Asn Met Asn Pro Leu Gly His Thr Arg Cys Pro Lys Tyr Val
        355                 360                 365

Arg Asn Arg Ile Gly Glu Ile Val Thr Ser His Gly Cys Gln Ile Tyr
370                 375                 380

Pro Glu Ser Ser Ser Ala Gly Leu Gly Asp Asp Pro Arg Pro Leu Tyr
385                 390                 395                 400

Thr Val Ala Phe Ser Ala Gln Glu Leu Trp Gly Asp Asp Gly Asn Gly
                405                 410                 415

Lys Asp Val Val Cys Val Asp Leu Trp Glu Pro Tyr Leu Ile Ser Ala
            420                 425                 430

<210> SEQ ID NO 15
<211> LENGTH: 303
<212> TYPE: PRT
<213> ORGANISM: Escherichia coli

<400> SEQUENCE: 15

Gln Met Ser Leu Gln Gln Glu Leu Arg Tyr Ile Glu Ala Leu Ser Ala
1               5                   10                  15

Ile Val Glu Thr Gly Gln Lys Met Leu Glu Ala Gly Glu Ser Ala Leu
                20                  25                  30

Asp Val Val Thr Glu Ala Val Arg Leu Leu Glu Glu Cys Pro Leu Phe
            35                  40                  45

Asn Ala Gly Ile Gly Ala Val Phe Thr Arg Asp Glu Thr His Glu Leu
        50                  55                  60

Asp Ala Cys Val Met Asp Gly Asn Thr Leu Lys Ala Gly Ala Val Ala
65                  70                  75                  80

Gly Val Ser His Leu Arg Asn Pro Val Leu Ala Ala Arg Leu Val Met
                85                  90                  95

```
Glu Gln Ser Pro His Val Met Met Ile Gly Glu Gly Ala Glu Asn Phe
            100                 105                 110

Ala Phe Ala Arg Gly Met Glu Arg Val Ser Pro Glu Ile Phe Ser Thr
            115                 120                 125

Ser Leu Arg Tyr Glu Gln Leu Leu Ala Ala Arg Lys Glu Gly Ala Arg
        130                 135                 140

Val Leu Asp His Ser Gly Ala Pro Leu Asp Glu Lys Gln Lys Met Gly
145                 150                 155                 160

Thr Val Gly Ala Val Ala Leu Asp Leu Asp Gly Asn Leu Ala Ala Ala
                165                 170                 175

Thr Ser Thr Gly Gly Met Thr Asn Lys Leu Pro Gly Arg Val Gly Asp
            180                 185                 190

Ser Pro Leu Val Gly Ala Gly Cys Tyr Ala Asn Asn Ala Ser Val Ala
        195                 200                 205

Val Ser Cys Thr Gly Thr Gly Glu Val Phe Ile Arg Ala Leu Ala Ala
210                 215                 220

Tyr Asp Ile Ala Ala Leu Met Asp Tyr Gly Gly Leu Ser Leu Ala Glu
225                 230                 235                 240

Ala Cys Glu Arg Val Val Met Glu Lys Leu Pro Thr Leu Gly Gly Ser
                245                 250                 255

Gly Gly Leu Ile Ala Ile Asp His Glu Gly Asn Val Ala Leu Pro Phe
            260                 265                 270

Asn Thr Glu Gly Met Tyr Arg Ala Trp Gly Tyr Ala Gly Asp Thr Pro
        275                 280                 285

Thr Thr Gly Ile Tyr Arg Glu Lys Gly Asp Thr Val Ala Thr Gln
290                 295                 300

<210> SEQ ID NO 16
<211> LENGTH: 348
<212> TYPE: PRT
<213> ORGANISM: Eriwinia chrysanthemi

<400> SEQUENCE: 16

Met Glu Arg Trp Phe Lys Ser Leu Phe Val Leu Val Leu Phe Phe Val
1               5                   10                  15

Phe Thr Ala Ser Ala Ala Asp Lys Leu Pro Asn Ile Val Ile Leu Ala
            20                  25                  30

Thr Gly Gly Thr Ile Ala Gly Ser Ala Ala Thr Gly Thr Gln Thr Thr
        35                  40                  45

Gly Tyr Lys Ala Gly Ala Leu Gly Val Asp Thr Leu Ile Asn Ala Val
    50                  55                  60

Pro Glu Val Lys Lys Leu Ala Asn Val Lys Gly Glu Gln Phe Ser Asn
65                  70                  75                  80

Met Ala Ser Glu Asn Met Thr Gly Asp Val Val Leu Lys Leu Ser Gln
                85                  90                  95

Arg Val Asn Glu Leu Leu Ala Arg Asp Asp Val Asp Gly Val Val Ile
            100                 105                 110

Thr His Gly Thr Asp Thr Val Glu Glu Ser Ala Tyr Phe Leu His Leu
        115                 120                 125

Thr Val Lys Ser Asp Lys Pro Val Val Phe Val Ala Ala Met Arg Pro
    130                 135                 140

Ala Thr Ala Ile Ser Ala Asp Gly Pro Met Asn Leu Leu Glu Ala Val
145                 150                 155                 160

Arg Val Ala Gly Asp Lys Gln Ser Arg Gly Arg Gly Val Met Val Val
```

```
                    165                 170                 175
Leu Asn Asp Arg Ile Gly Ser Ala Arg Tyr Ile Thr Lys Thr Asn Ala
            180                 185                 190

Ser Thr Leu Asp Thr Phe Lys Ala Asn Glu Glu Gly Tyr Leu Gly Val
        195                 200                 205

Ile Ile Gly Asn Arg Ile Tyr Tyr Gln Asn Arg Ile Asp Lys Leu His
    210                 215                 220

Thr Thr Arg Ser Val Phe Asp Val Arg Gly Leu Thr Ser Leu Pro Lys
225                 230                 235                 240

Val Asp Ile Leu Tyr Gly Tyr Gln Asp Pro Glu Tyr Leu Tyr Asp
                245                 250                 255

Ala Ala Ile Gln His Gly Val Lys Gly Ile Val Tyr Ala Gly Met Gly
            260                 265                 270

Ala Gly Ser Val Ser Val Arg Gly Ile Ala Gly Met Arg Lys Ala Met
        275                 280                 285

Glu Lys Gly Val Val Ile Arg Ser Thr Arg Thr Gly Asn Gly Ile
290                 295                 300

Val Pro Pro Asp Glu Glu Leu Pro Gly Leu Val Ser Asp Ser Leu Asn
305                 310                 315                 320

Pro Ala His Ala Arg Ile Leu Met Leu Ala Leu Thr Arg Thr Ser
                325                 330                 335

Asp Pro Lys Val Ile Gln Glu Tyr Phe His Thr Tyr
            340                 345

<210> SEQ ID NO 17
<211> LENGTH: 281
<212> TYPE: PRT
<213> ORGANISM: Rhodococcus rhodochrous

<400> SEQUENCE: 17

Leu Ser Val Glu Leu Val Glu Val Val Arg Ser Gly Phe Arg Glu Cys
1               5                   10                  15

Val His Arg Gly Ser Leu Val Val Leu Asp Pro Ala Gly Asp Val Arg
            20                  25                  30

Leu Ala Leu Gly Glu Ile Arg Thr Pro Ile Tyr Pro Arg Ser Ser Asn
        35                  40                  45

Lys Pro Leu Gln Ala Val Ala Leu Leu Arg Gln Gly Phe Val Pro Arg
    50                  55                  60

Ser Thr Glu Glu Leu Ala Ile Ala Thr Ala Ser His Glu Gly Glu Ala
65                  70                  75                  80

Gly His Val Arg Leu Val Glu Ala Leu Leu Ala Gly His Gly Phe Thr
                85                  90                  95

Glu Asp Asp Leu Gln Cys Pro Pro Asp Leu Pro Gly Asn Glu Pro Ala
            100                 105                 110

Arg Ala Thr Ile Val Ala Ala Gly His Pro Arg Arg Thr Val Tyr Met
        115                 120                 125

Asn Cys Ser Gly Lys His Ala Ala Met Leu Ala Thr Cys Ala Ala Asn
    130                 135                 140

Gly Trp Pro Val Arg Ala Gly Ala Asp Glu Pro Gly Tyr Leu Asp Ser
145                 150                 155                 160

Ala His Pro Leu Gln Gln Ala Val Val Glu Thr Val Leu Asp Leu Ala
                165                 170                 175

Gly Asp Val Glu Asp Thr Asp Leu Gly Ile Asp Gly Cys Gly Leu Pro
            180                 185                 190
```

```
Ile Val Pro Leu Pro Leu Val Asn Leu Ala Arg Ala Tyr Ser Arg Leu
            195                 200                 205

Ala Thr Ala Gly Pro Gly Thr Pro Glu Arg Ala Val Ala Asp Ala Ile
        210                 215                 220

Arg Ser His Pro His Leu Val Ser Gly Thr Gly Lys Asp Asp Ala Arg
225                 230                 235                 240

Leu Met Pro Ala Val Pro Gly Leu Leu Cys Lys Ala Gly Ala Asp Gly
                245                 250                 255

Val His Ala Gly Ala Leu Pro Asp Gly Thr Ala Phe Ala Leu Lys Ile
            260                 265                 270

Asp Asp Gly His Glu Arg Ala Arg Leu
            275                 280

<210> SEQ ID NO 18
<211> LENGTH: 340
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = any amino acid
<220> FEATURE:
<221> NAME/KEY: MISC_FEATURE
<222> LOCATION: (26)..(26)
<223> OTHER INFORMATION: Xaa = any amino acid
<220> FEATURE:
<221> NAME/KEY: MISC_FEATURE
<222> LOCATION: (33)..(33)
<223> OTHER INFORMATION: Xaa = any amino acid
<220> FEATURE:
<221> NAME/KEY: MISC_FEATURE
<222> LOCATION: (36)..(37)
<223> OTHER INFORMATION: Xaa = any amino acid
<220> FEATURE:
<221> NAME/KEY: MISC_FEATURE
<222> LOCATION: (52)..(52)
<223> OTHER INFORMATION: Xaa = any amino acid
<220> FEATURE:
<221> NAME/KEY: MISC_FEATURE
<222> LOCATION: (54)..(55)
<223> OTHER INFORMATION: Xaa = any amino acid
<220> FEATURE:
<221> NAME/KEY: MISC_FEATURE
<222> LOCATION: (61)..(61)
<223> OTHER INFORMATION: Xaa = any amino acid
<220> FEATURE:
<221> NAME/KEY: MISC_FEATURE
<222> LOCATION: (64)..(65)
<223> OTHER INFORMATION: Xaa = any amino acid
<220> FEATURE:
<221> NAME/KEY: MISC_FEATURE
<222> LOCATION: (69)..(69)
<223> OTHER INFORMATION: Xaa = any amino acid
<220> FEATURE:
<221> NAME/KEY: MISC_FEATURE
<222> LOCATION: (93)..(93)
<223> OTHER INFORMATION: Xaa = any amino acid
<220> FEATURE:
<221> NAME/KEY: MISC_FEATURE
```

```
<222> LOCATION: (99)..(99)
<223> OTHER INFORMATION: Xaa = any amino acid
<220> FEATURE:
<221> NAME/KEY: MISC_FEATURE
<222> LOCATION: (128)..(130)
<223> OTHER INFORMATION: Xaa = any amino acid
<220> FEATURE:
<221> NAME/KEY: MISC_FEATURE
<222> LOCATION: (132)..(132)
<223> OTHER INFORMATION: Xaa = any amino acid
<220> FEATURE:
<221> NAME/KEY: MISC_FEATURE
<222> LOCATION: (134)..(136)
<223> OTHER INFORMATION: Xaa = any amino acid
<220> FEATURE:
<221> NAME/KEY: MISC_FEATURE
<222> LOCATION: (143)..(143)
<223> OTHER INFORMATION: Xaa = any amino acid
<220> FEATURE:
<221> NAME/KEY: MISC_FEATURE
<222> LOCATION: (149)..(149)
<223> OTHER INFORMATION: Xaa = any amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: MISC_FEATURE
<222> LOCATION: (157)..(157)
<223> OTHER INFORMATION: Xaa = any amino acid
<220> FEATURE:
<221> NAME/KEY: MISC_FEATURE
<222> LOCATION: (160)..(160)
<223> OTHER INFORMATION: Xaa = any amino acid
<220> FEATURE:
<221> NAME/KEY: MISC_FEATURE
<222> LOCATION: (161)..(164)
<223> OTHER INFORMATION: Xaa = any amino acid
<220> FEATURE:
<221> NAME/KEY: MISC_FEATURE
<222> LOCATION: (169)..(169)
<223> OTHER INFORMATION: Xaa = any amino acid
<220> FEATURE:
<221> NAME/KEY: MISC_FEATURE
<222> LOCATION: (172)..(172)
<223> OTHER INFORMATION: Xaa = any amino acid
<220> FEATURE:
<221> NAME/KEY: MISC_FEATURE
<222> LOCATION: (176)..(176)
<223> OTHER INFORMATION: Xaa = any amino acid
<220> FEATURE:
<221> NAME/KEY: MISC_FEATURE
<222> LOCATION: (180)..(180)
<223> OTHER INFORMATION: Xaa = any amino acid
<220> FEATURE:
<221> NAME/KEY: MISC_FEATURE
<222> LOCATION: (184)..(184)
<223> OTHER INFORMATION: Xaa = any amino acid
<220> FEATURE:
<221> NAME/KEY: MISC_FEATURE
<222> LOCATION: (189)..(189)
<223> OTHER INFORMATION: Xaa = any amino acid
<220> FEATURE:
<221> NAME/KEY: MISC_FEATURE
<222> LOCATION: (193)..(194)
<223> OTHER INFORMATION: Xaa = any amino acid
<220> FEATURE:
<221> NAME/KEY: MISC_FEATURE
<222> LOCATION: (208)..(208)
<223> OTHER INFORMATION: Xaa = any amino acid
<220> FEATURE:
<221> NAME/KEY: MISC_FEATURE
<222> LOCATION: (211)..(211)
<223> OTHER INFORMATION: Xaa = any amino acid
<220> FEATURE:
<221> NAME/KEY: MISC_FEATURE
<222> LOCATION: (213)..(214)
<223> OTHER INFORMATION: Xaa = any amino acid
<220> FEATURE:
```

```
<221> NAME/KEY: MISC_FEATURE
<222> LOCATION: (218)..(218)
<223> OTHER INFORMATION: Xaa = any amino acid
<220> FEATURE:
<221> NAME/KEY: MISC_FEATURE
<222> LOCATION: (220)..(220)
<223> OTHER INFORMATION: Xaa = any amino acid
<220> FEATURE:
<221> NAME/KEY: MISC_FEATURE
<222> LOCATION: (225)..(226)
<223> OTHER INFORMATION: Xaa = any amino acid
<220> FEATURE:
<221> NAME/KEY: MISC_FEATURE
<222> LOCATION: (234)..(236)
<223> OTHER INFORMATION: Xaa = any amino acid
<220> FEATURE:
<221> NAME/KEY: MISC_FEATURE
<222> LOCATION: (242)..(244)
<223> OTHER INFORMATION: Xaa = any amino acid
<220> FEATURE:
<221> NAME/KEY: MISC_FEATURE
<222> LOCATION: (248)..(248)
<223> OTHER INFORMATION: Xaa = any amino acid
<220> FEATURE:
<221> NAME/KEY: MISC_FEATURE
<222> LOCATION: (252)..(254)
<223> OTHER INFORMATION: Xaa = any amino acid
<220> FEATURE:
<221> NAME/KEY: MISC_FEATURE
<222> LOCATION: (257)..(260)
<223> OTHER INFORMATION: Xaa = any amino acid
<220> FEATURE:
<221> NAME/KEY: misc_feature
<222> LOCATION: (278)..(279)
<223> OTHER INFORMATION: Xaa can be any naturally occurring amino acid
<220> FEATURE:
<221> NAME/KEY: MISC_FEATURE
<222> LOCATION: (285)..(286)
<223> OTHER INFORMATION: Xaa = any amino acid
<220> FEATURE:
<221> NAME/KEY: MISC_FEATURE
<222> LOCATION: (289)..(289)
<223> OTHER INFORMATION: Xaa = any amino acid
<220> FEATURE:
<221> NAME/KEY: MISC_FEATURE
<222> LOCATION: (292)..(292)
<223> OTHER INFORMATION: Xaa = any amino acid
<220> FEATURE:
<221> NAME/KEY: MISC_FEATURE
<222> LOCATION: (307)..(307)
<223> OTHER INFORMATION: Xaa = any amino acid
<220> FEATURE:
<221> NAME/KEY: MISC_FEATURE
<222> LOCATION: (309)..(309)
<223> OTHER INFORMATION: Xaa = any amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: MISC_FEATURE
<222> LOCATION: (314)..(315)
<223> OTHER INFORMATION: Xaa = any amino acid
<220> FEATURE:
<221> NAME/KEY: MISC_FEATURE
<222> LOCATION: (317)..(317)
<223> OTHER INFORMATION: Xaa = any amino acid
<220> FEATURE:
<221> NAME/KEY: MISC_FEATURE
<222> LOCATION: (320)..(320)
<223> OTHER INFORMATION: Xaa = any amino acid
<220> FEATURE:
<221> NAME/KEY: MISC_FEATURE
<222> LOCATION: (326)..(327)
<223> OTHER INFORMATION: Xaa = any amino acid
<220> FEATURE:
<221> NAME/KEY: MISC_FEATURE
<222> LOCATION: (332)..(332)
<223> OTHER INFORMATION: Xaa = any amino acid
```

```
<220> FEATURE:
<221> NAME/KEY: MISC_FEATURE
<222> LOCATION: (337)..(340)
<223> OTHER INFORMATION: Xaa = any amino acid

<400> SEQUENCE: 18
```

| | | | | | | | | | | | | | | |
|---|---|---|---|---|---|---|---|---|---|---|---|---|---|---|
| Met | Ser | Xaa | Ala | Arg | Xaa | Ala | Ile | Glu | Ala | Leu | Leu | Val | Glu | Xaa | Gly |
| 1 | | | | 5 | | | | | 10 | | | | | 15 | |

Leu Ile Thr Xaa Glu Ala Val Asp Arg Xaa Ser Ser Val Val Glu Asn
            20                  25                  30

Xaa Val Gly Xaa Xaa Ile Gly Ala Lys Ile Val Ala Arg Ser Trp Val
        35                  40                  45

Asp Pro Glu Xaa Ala Xaa Xaa Leu Leu Glu Asp Ala Xaa Ala Ala Xaa
    50                  55                  60

Xaa Glu Leu Gly Xaa Ala Gly Gln Gly Glu Gln Ser Ala Val Phe Asn
65              70                  75                  80

Glu Asp Glu Thr His His Val Val Cys Thr Leu Xaa Ala Ser Cys
                85                  90                  95

Tyr Pro Xaa Pro Val Leu Gly Leu Pro Pro Asp Trp Tyr Lys Asn Pro
            100                 105                 110

Ala Tyr Arg Ala Arg Leu Val Ala Asp Pro Arg Pro Gly Val Leu Xaa
            115                 120                 125

Xaa Xaa Phe Xaa Phe Xaa Xaa Xaa Leu Glu Val Glu Val Arg Xaa Trp
130             135                 140

Asp Ser Ser Ala Xaa Leu Arg Tyr Xaa Val Leu Pro Xaa Arg Pro Xaa
145             150                 155                 160

Gly Xaa Xaa Xaa Val Thr Glu Thr Xaa Leu Ala Xaa Leu Asp Thr Xaa
            165                 170                 175

Asp Ser Met Xaa Gly Val Ser Xaa Gly Thr Thr Pro Xaa Val Ala Leu
            180                 185                 190

Xaa Xaa Asp Gly Ser Ile His Asp Thr Gly Gly Met Thr Gly Leu Xaa
        195                 200                 205

Pro Val Xaa Val Xaa Xaa Asp Glu Pro Xaa Phe Xaa Ala Gly Trp Glu
    210                 215                 220

Xaa Xaa Val Leu Ser Ile Ala Val Ala Xaa Xaa Ala Gly Arg Val
225             230                 235                 240

Phe Xaa Xaa Xaa Ile Asp Ala Xaa Met Arg Lys Xaa Xaa Xaa Asp Gly
        245                 250                 255

Xaa Xaa Xaa Xaa Glu Glu Arg Arg Val Gln Glu Leu Pro Asp Pro Leu
        260                 265                 270

Ile Glu Ile Thr His Xaa Xaa Asn Gly Ala Leu Pro Xaa Xaa Thr Glu
            275                 280                 285

Xaa Ala Phe Xaa Val Gly Asp Lys Val Arg Gly Tyr Val Arg Arg Ala
    290                 295                 300

Gly Asp Xaa Pro Xaa His Xaa Tyr Thr Xaa Xaa Phe Xaa Ala Thr Xaa
305             310                 315                 320

Leu Trp Gly Glu Pro Xaa Xaa Val Val Asp Val Xaa Glu Pro Tyr Leu
            325                 330                 335

Xaa Xaa Xaa Xaa
        340

```
<210> SEQ ID NO 19
<211> LENGTH: 203
<212> TYPE: PRT
<213> ORGANISM: Rhodococcus rhodochrous
```

-continued

```
<400> SEQUENCE: 19

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
50                  55                  60

Trp Leu Glu Glu Asp Ala Thr Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 20
<211> LENGTH: 203
<212> TYPE: PRT
<213> ORGANISM: Rhodococcus rhodochrous

<400> SEQUENCE: 20

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
50                  55                  60

Trp Leu Glu Glu Asp Ala Thr Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Glu Ile
145                 150                 155                 160
```

```
Arg Tyr Ile Val Ile Pro Glu Arg Pro Ala Gly Thr Asp Gly Trp Ser
            165                 170                 175

Glu Asp Glu Leu Ala Lys Leu Val Ser Arg Asp Ser Met Ile Gly Val
        180                 185                 190

Ser Asn Ala Leu Thr Pro Gln Glu Val Ile Val
        195                 200

<210> SEQ ID NO 21
<211> LENGTH: 203
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (178)..(178)
<223> OTHER INFORMATION: Xaa = any amino acid
<220> FEATURE:
<221> NAME/KEY: MISC_FEATURE
<222> LOCATION: (181)..(181)
<223> OTHER INFORMATION: Xaa = any amino acid

<400> SEQUENCE: 21

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Glu Asn Glu Ile Gly Pro Met Gly
        35                  40                  45

Gly Ala Lys Val Val Ala Lys Ser Trp Val Asp Pro Glu Tyr Arg Lys
50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
            165                 170                 175

Glu Xaa Glu Leu Xaa Lys Leu Val Ser Arg Asp Ser Met Ile Gly Val
        180                 185                 190

Ser Asn Ala Leu Thr Pro Gln Glu Val Ile Val
        195                 200

<210> SEQ ID NO 22
<211> LENGTH: 229
<212> TYPE: PRT
<213> ORGANISM: Rhodococcus rhodochrous

<400> SEQUENCE: 22

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30
```

```
Thr Leu Ser Ile Leu Thr Trp Met His Leu Lys Gly Ile Ser Trp Trp
            35                  40                  45

Asp Lys Ser Arg Phe Phe Arg Glu Ser Met Gly Asn Glu Asn Tyr Val
 50                  55                  60

Asn Glu Ile Arg Asn Ser Tyr Tyr Thr His Trp Leu Ser Ala Ala Glu
 65                  70                  75                  80

Arg Ile Leu Val Ala Asp Lys Ile Ile Thr Glu Glu Arg Lys His
                 85                  90                  95

Arg Val Gln Glu Ile Leu Glu Gly Arg Tyr Thr Asp Arg Lys Pro Ser
                100                 105                 110

Arg Lys Phe Asp Pro Ala Gln Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ala Gly Leu Gly Asp Asp
            180                 185                 190

Pro Arg Pro Leu Tyr Thr Val Ala Phe Ser Ala Gln Glu Leu Trp Gly
            195                 200                 205

Asp Asp Gly Asn Gly Lys Asp Val Val Cys Val Asp Leu Trp Glu Pro
        210                 215                 220

Tyr Leu Ile Ser Ala
225

<210> SEQ ID NO 23
<211> LENGTH: 229
<212> TYPE: PRT
<213> ORGANISM: Rhodococcus rhodochrous

<400> SEQUENCE: 23

Met Asp Gly Ile His Asp Thr Gly Gly Met Thr Gly Tyr Gly Pro Val
 1               5                  10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Met Ser Trp Trp
            35                  40                  45

Asp Lys Ser Arg Phe Phe Arg Glu Ser Met Gly Asn Glu Asn Tyr Val
 50                  55                  60

Asn Glu Ile Arg Asn Ser Tyr Tyr Thr His Trp Leu Ser Ala Ala Glu
 65                  70                  75                  80

Arg Ile Leu Val Ala Asp Lys Ile Ile Thr Glu Glu Arg Lys His
                 85                  90                  95

Arg Val Gln Glu Ile Leu Glu Gly Arg Tyr Thr Asp Arg Asn Pro Ser
                100                 105                 110

Arg Lys Phe Asp Pro Ala Glu Ile Glu Lys Ala Ile Glu Arg Leu His
            115                 120                 125

Glu Pro His Ser Leu Val Leu Pro Gly Ala Glu Pro Ser Phe Ser Leu
        130                 135                 140

Gly Asp Lys Val Lys Val Lys Asn Met Asn Pro Leu Gly His Thr Arg
145                 150                 155                 160

Cys Pro Lys Tyr Val Arg Asn Arg Ile Gly Glu Ile Val Thr Ser His
                165                 170                 175
```

```
                  165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
210                 215                 220

Tyr Leu Ile Ser Ala
225

<210> SEQ ID NO 24
<211> LENGTH: 229
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (45)..(45)
<223> OTHER INFORMATION: Xaa = any amino acid
<220> FEATURE:
<221> NAME/KEY: MISC_FEATURE
<222> LOCATION: (110)..(110)
<223> OTHER INFORMATION: Xaa = any amino acid
<220> FEATURE:
<221> NAME/KEY: MISC_FEATURE
<222> LOCATION: (119)..(119)
<223> OTHER INFORMATION: Xaa = any amino acid
<220> FEATURE:
<221> NAME/KEY: MISC_FEATURE
<222> LOCATION: (134)..(134)
<223> OTHER INFORMATION: Xaa = any amino acid
<220> FEATURE:
<221> NAME/KEY: MISC_FEATURE
<222> LOCATION: (148)..(148)
<223> OTHER INFORMATION: Xaa = any amino acid
<220> FEATURE:
<221> NAME/KEY: MISC_FEATURE
<222> LOCATION: (152)..(152)
<223> OTHER INFORMATION: Xaa = any amino acid
<220> FEATURE:
<221> NAME/KEY: MISC_FEATURE
<222> LOCATION: (168)..(168)
<223> OTHER INFORMATION: Xaa = any amino acid
<220> FEATURE:
<221> NAME/KEY: MISC_FEATURE
<222> LOCATION: (175)..(175)
<223> OTHER INFORMATION: Xaa = any amino acid

<400> SEQUENCE: 24

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Xaa Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Xaa Pro Ser
            100                 105                 110

Arg Lys Phe Asp Pro Ala Xaa Ile Glu Lys Ala Ile Glu Arg Leu His
        115                 120                 125
```

-continued

```
Glu Pro His Ser Leu Xaa Leu Pro Gly Ala Glu Pro Ser Phe Ser Leu
    130             135             140

Gly Asp Lys Xaa Lys Val Lys Xaa Met Asn Pro Leu Gly His Thr Arg
145             150             155                         160

Cys Pro Lys Tyr Val Arg Asn Xaa Ile Gly Glu Ile Val Thr Xaa His
                165             170                 175

Gly Cys Gln Ile Tyr Pro Glu Ser Ser Ser Ala Gly Leu Gly Asp Asp
            180             185                 190

Pro Arg Pro Leu Tyr Thr Val Ala Phe Ser Ala Gln Glu Leu Trp Gly
        195             200                 205

Asp Asp Gly Asn Gly Lys Asp Val Val Cys Val Asp Leu Trp Glu Pro
    210             215                 220

Tyr Leu Ile Ser Ala
225
```

ENDOTOXIN FREE ASPARAGINASE

CROSS-REFERENCE TO RELATED APPLICATIONS

This application claims benefit of U.S. Provisional Application No. 62/417,456, filed Nov. 4, 2016, which is hereby incorporated herein by reference in its entirety.

BACKGROUND

Asparaginase enzymes are used in the treatment of juvenile Acute Lymphoblastic Leukemia (ALL). ALL cells are unable to synthesize the amino acid asparagine and are dependent upon exogenous sources of this amino acid. When exposed to asparaginase, the asparagine in ALL cells is significantly reduced. Because these cells cannot by themselves replenish their asparagine pool, the ALL cells become stressed and more sensitive to chemotherapy.

Asparaginase preparations currently used in the treatment of juvenile ALL are either derived and produced from *E. coli* or *Erwinia* or are recombinant proteins originating in either *E. coli* or *Erwinia* which are produced in either *E. coli* or *Erwinia*. Whether native or recombinant, *E. coli* or *Erwina* asparaginase is a homo-tetramer. It is an inherent property that proteins from Gram-negative bacteria are contaminated with endotoxin. Recombinant proteins produced in Gram-negative hosts typically show enhanced levels of endotoxin. This is particular true when the cells are over-induced and/or when high-cell density fermentation is attempted.

Used since the 1960s, the current treatment regimes of juvenile ALL employing asparaginase show a success rate of 92% (5-year survival). The 8% of patients that do not respond positively to asparaginase is thought to be due to sensitivity to the asparaginase. Asparaginase from *E. coli* or *Erwinia* is not used in the treatment of adult ALL because longer-treatment courses required typically result in sensitivity and adverse reactions due in part due to traces of endotoxin.

SUMMARY

Disclosed herein are asparaginase enzymes that, being produced/derived from the Gram-positive bacterium *Rhodococcus rhodochrous* DAP 96253, are endotoxin free. *R. rhodochrous* DAP 96253 is shown herein to produce a classic L-asparaginase enzyme that has a substantially unique primary and secondary structure than those produced from *E. coli* and *E. coli* or *Erwinia* spp. *R. rhodochrous* DAP 96253 is also shown herein to produce at least one Nitrile Hydratase (NHase) that, in addition to having nitrile hydratase activity, also shows asparaginase activity. The disclosed NHase enzymes with asparaginase activity are therefore also referred herein as a "NHase-Asparaginase" to distinguish this enzyme from the classic asparaginase also produced by in *R. rhodochrous* DAP 96253. However, these enzymes are individually and collectively referred to herein as "endotoxin-free asparaginase enzymes."

Also disclosed are methods of using the disclosed endotoxin-free asparaginase enzymes to treat subjects with a disease treatable by depletion of asparagine. For example, the disclosed endotoxin-free asparaginase enzymes are useful in the treatment or the manufacture of a medicament for use in the treatment of acute lymphoblastic leukemia (ALL) in both adults and children, as well as other conditions where asparagine depletion is expected to have a useful effect. The disclosed endotoxin-free asparaginase enzymes are endotoxin free. The fermentation yields of the endotoxin-free asparaginase enzymes are several orders of magnitude better than published sources for the enteric bacteria derived asparaginases.

Disclosed herein is a method for treating a subject with a disease treatable by L-asparagine depletion, comprising administering to the subject a composition an endotoxin-free asparaginase enzyme disclosed herein.

In some embodiments, the endotoxin-free asparaginase enzyme is a low mass NHase-Asparaginase comprising a heteropolymer of a polypeptide having an amino acid sequence with at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:2 and a polypeptide having an amino acid sequence with at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:4.

In some embodiments, the endotoxin-free asparaginase enzyme is a high mass NHase-Asparaginase comprising hetero polymer enzyme of a polypeptide having an amino acid sequence with at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:6 and a polypeptide having an amino acid sequence with at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:8.

In some embodiments, the endotoxin-free asparaginase enzyme is a classic L-asparaginase having an amino acid sequence with at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:10.

In some embodiments, the endotoxin-free asparaginase enzyme is a recombinant asparaginase. In other embodiments, the endotoxin-free asparaginase enzyme is isolated from *Rhodococcus rhodochrous* DAP 96253 cells.

In particular, the endotoxin-free asparaginase enzyme can be isolated from DAP 96253 cells that have been induced to produce the asparaginase using an inducing agent selected from the group consisting of urea, methyl carbamate, methacrylamide, acetamide, cobalt, asparagine or asparagine derivative, and combinations thereof.

In some embodiments, the disclosed endotoxin-free asparaginase enzyme is stabilized by conjugating it to a polyethylene glycol (PEG). For example, the PEG can have a molecular weight of about 1000 to 5000 Da. In some embodiments, the PEG is covalently linked to one or more amino groups of the endotoxin-free asparaginase enzyme, e.g. by an amide bond.

The disclosed endotoxin-free asparaginase enzyme can be used to treat any disease treatable by L-asparagine depletion. In some cases, the disease is a cancer, such as a cancer selected from the group consisting of Acute Lymphoblastic Leukemia ("ALL"), non-Hodgkin's lymphoma, NK lymphoma, and pancreatic cancer. In particular embodiments, the endotoxin-free asparaginase enzyme can be used to treat juvenile ALL and adult ALL.

In some embodiments, the endotoxin-free asparaginase enzyme can be used to treat a subject who has had a previous hypersensitivity to an *E. coli* L-aspariginase or *Erwinia* L-asparaginase.

Also disclosed is a method for catalyzing the hydrolysis of asparagine in a sample to aspartic acid that comprises contacting the sample with a composition comprising an endotoxin-free asparaginase disclosed herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a table comparing 1) cobalt-containing low-mass nitrile hydratase subunit alpha and beta from *R. rhodochrous* DAP 96253, 2) cobalt-containing high-mass nitrile hydratase subunit alpha and beta from *R. rhodochrous* DAP 96253, 3) Elspar® asparaginase, 4) asparaginase aminohydralase *E. chrysanthemi*, and 5) classic L-asparaginase from *R. rhodochrous* DAP 96253. Upper comparison is the percentage of identical residues in alignment positions to overlapping alignment positions between the two sequences. Lower comparison is the number of alignment positions where one sequence is different from the other. This includes gap differences as in the Gaps comparison.

DETAILED DESCRIPTION

Figure 1:
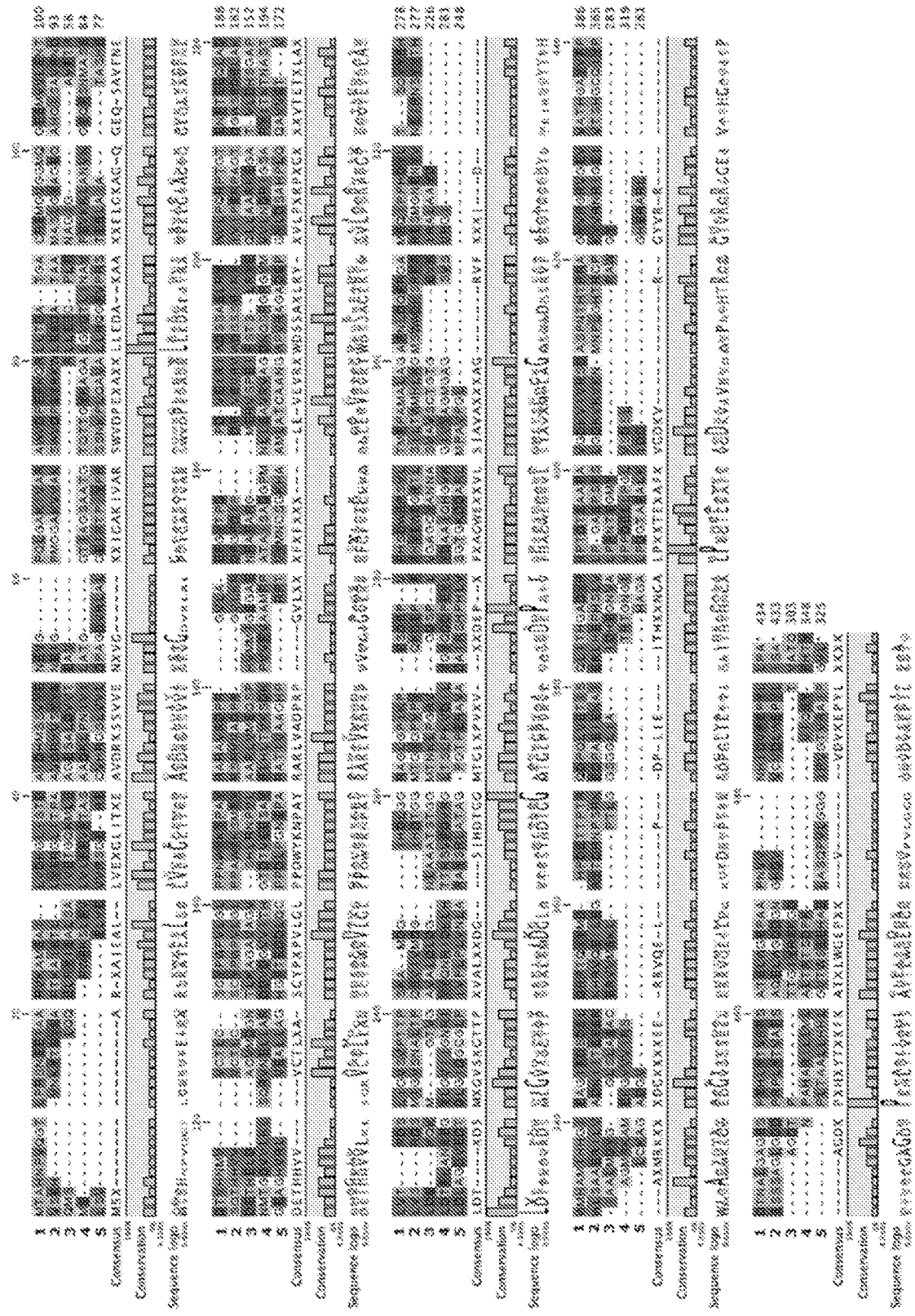
FIG. 1 is a sequence alignment of 1) cobalt-containing low-mass nitrile hydratase subunit-alpha and -beta from *R. rhodochrous* DAP 96253 (SEQ ID NO:13), 2) cobalt-containing high-mass nitrile hydratase subunit-alpha and -beta from *R. rhodochrous* DAP 96253 (SEQ ID NO:14), 3) Elspar® asparaginase (SEQ ID NO:15), 4) asparaginase aminohydralase *E. chrysanthemi* (SEQ ID NO:16), and 5) classic L-asparaginase from *R. rhodochrous* DAP 96253 (SEQ ID NO:17). Also shown is a consensus sequence (SEQ ID NO:18).
Figure 3:
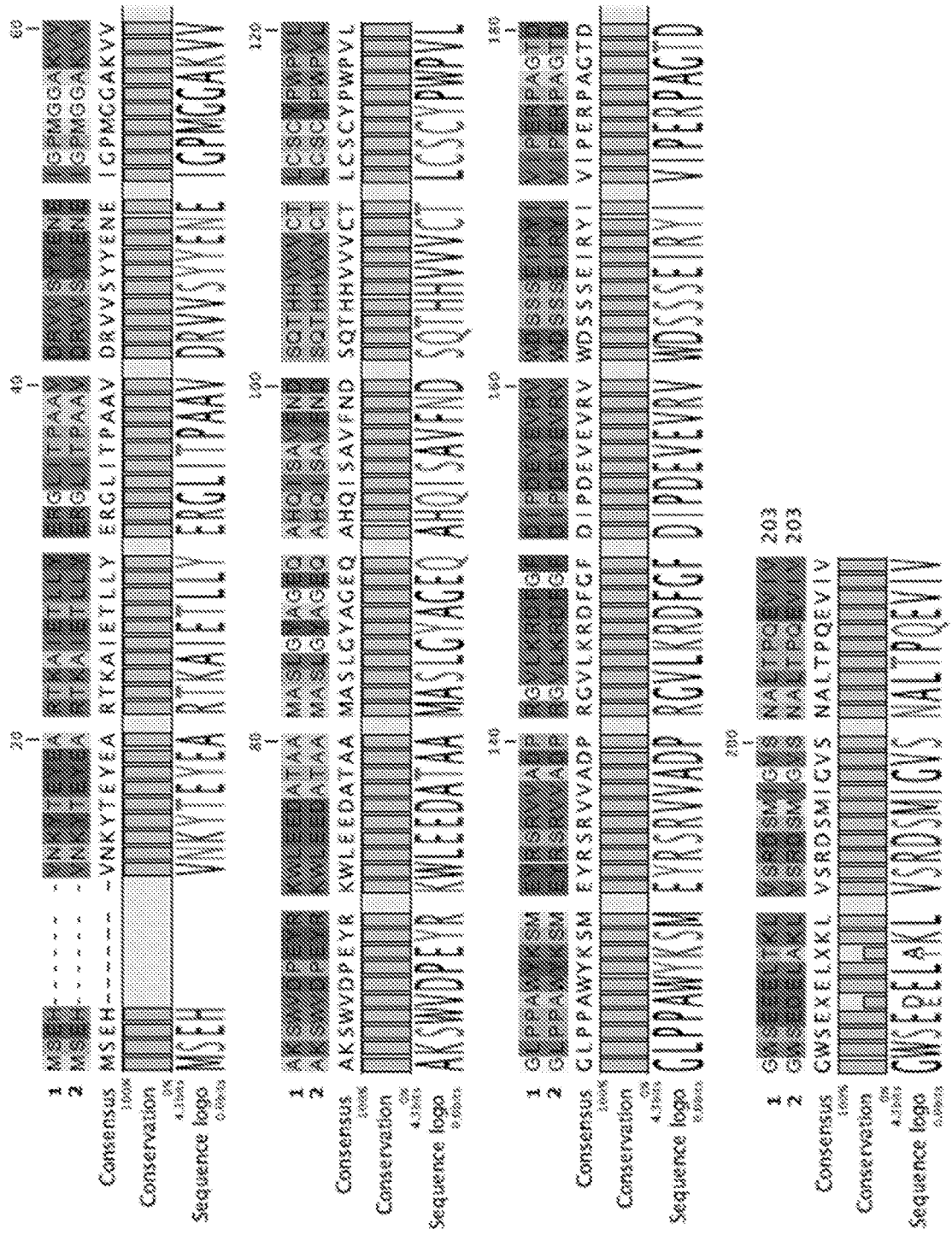
FIG. 3 is a sequence alignment of 1) *R. rhodochrous* J1 nitrile hydratase alpha (SEQ ID NO:19) and 2) cobalt-containing nitrile hydratase subunit alpha from *R. rhodochrous* DAP 96253 (SEQ ID NO:20). Also shown is a consensus sequence (SEQ ID NO:21).
Figure 4:
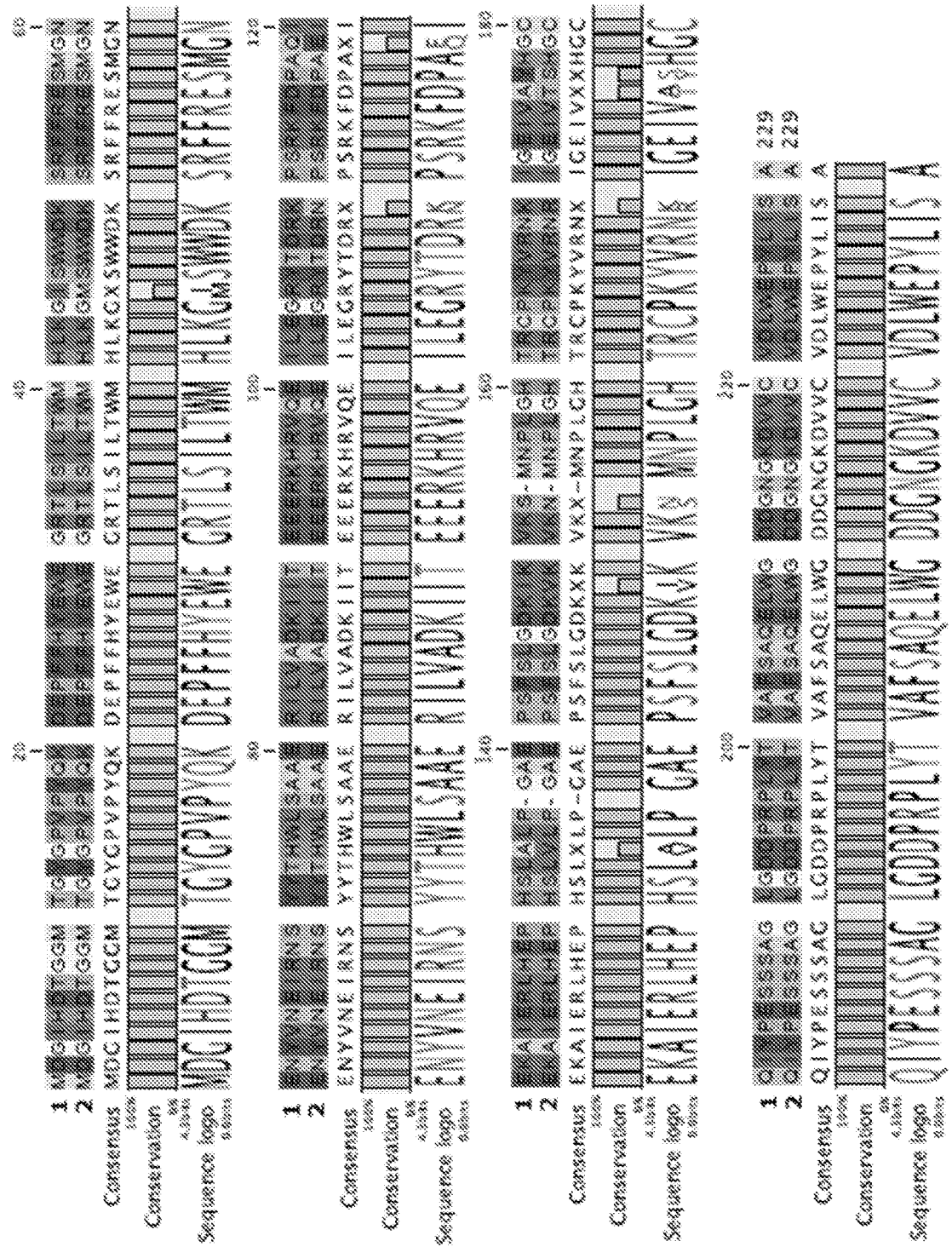
FIG. 4 is a sequence alignment of 1) *R. rhodochrous* J1 nitrile hydratase beta (SEQ ID NO:22) and 2) cobalt-containing nitrile hydratase subunit beta from *R. rhodochrous* DAP 96253 (SEQ ID NO:23). Also shown is a consensus sequence (SEQ ID NO:24).

As used herein, the singular forms "a", "an", "the", include plural referents unless the context clearly dictates otherwise.

Throughout the specification the word "comprising," or grammatical variations thereof, will be understood to imply the inclusion of a stated element, integer or step, or group of elements, integers or steps, but not the exclusion of any other element, integer or step, or group of elements, integers or steps.

The disclosed compositions, apparatuses, and methods arise from the discovery that induced cells of *Rhodococcus rhodochrous* DAP 96253 have significant levels of an asparaginase enzyme (NHase-Asparaginase) that is substantially different from enteric asparaginase, and contains no endotoxin.

Asparaginase is well documented in Gram-negative bacteria, and especially in *Escherichia coli* and in *Erwinia* spp. Sequencing of the α- and β-subunits of the disclosed endotoxin-free asparaginase enzymes show that the sequence of these subunits are unlike the sequence(s) seen in asparaginase obtained from other bacteria (including both Gram-negative, Gram-positive). Thus the primary structures of the disclosed endotoxin-free asparaginase enzymes are unique.

In both *E. coli* and in *Erwinia*, active asparaginase is a homo-dimer (where two intimate homo-dimers become intimately associated). In contrast, the high-mass NHase-asparaginase can be composed of at least 8 α-subunits and at least 8 β-subunits (i.e., at least a 16 mer). In the high-mass NHase-asparaginase, the α- and β-subunits are essentially in parity (i.e., 1:1 ratio). Furthermore this enzyme contains non-corrin-Cobalt at the active site. Thus, the secondary, tertiary and quaternary structure of the classic asparaginase seen in Gram-negative bacteria are very much different than the disclosed high-mass NHase-asparaginase.

During induction of *R. rhodochrous* DAP 96253 during fermentation, the high levels of NHase (>150 units/mg-cell dry weight, typically 200-600 units) also show higher levels of asparaginase (20-30 units/mg-cell dry weight) than the levels of asparaginase activity reported in *E. coli* or *Erwinia*. When it is considered that it is possible to obtain greater than 50 grams of cells per liter, which is considerably higher than that seen in *E. coli* or *Erwinia*, the amount of asparaginase activity produced per liter is order of magnitudes higher for the disclosed endotoxin-free asparaginase enzymes.

The disclosed endotoxin-free asparaginase enzymes can be used in any indication for which prior asparaginase enzymes were being used. For example, asparaginase from Gram-negative sources has been suggested for use in reducing acrylamide in food preparations. As asparaginase obtained from Gram-negative bacteria will contain endotoxin, the use of these asparaginase enzymes in food is problematic. The disclosed endotoxin-free asparaginase enzymes do not contain endotoxin and therefore can be used safely to reduce acrylamide in prepared foods.

Asparaginase Sources

In some embodiments, the disclosed endotoxin-free asparaginase enzymes are isolated from a *Rhodococcus* spp. bacteria, such as, for example, *Rhodococcus rhodochrous* DAP 96253 strain, *Rhodococcus rhodochrous* DAP 96622 strain, or combinations thereof.

In certain embodiments, the bacteria is "induced" to express the disclosed endotoxin-free asparaginase enzymes by exposure or treatment with a suitable inducing agent. Inducing agents include, but are not limited to urea, methyl carbamate, cobalt, asparagine, glutamine, and combinations thereof. Optionally, the one or more bacteria are exposed to or treated with urea, methyl carbamate, methacrylamide, or acetamide.

The inducing agent, when used, can be added at any time during cultivation of the desired cells. For example, with respect to bacteria, the culture medium can be supplemented with an inducing agent prior to beginning cultivation of the bacteria. Alternately, the bacteria could be cultivated on a medium for a predetermined amount of time to grow the bacteria and the inducing agent could be added at one or more predetermined times to induce endotoxin-free asparaginase enzymes in the bacteria. Moreover, the inducing agent could be added to the growth medium (or to a separate mixture including the previously grown bacteria) to induce endotoxin-free asparaginase enzymes in the bacteria after the growth of the bacteria is completed or during a second growth or maintenance phase.

The methods of inducing an enzymatic activity can be accomplished without the requirement of introducing hazardous nitriles, such as acrylonitrile, into the environment. Previously, it was believed that induction of specific enzyme activity in certain microorganisms required the addition of chemical inducers. For example, in the induction of nitrile hydratase activity in *Rhodococcus rhodochrous* and *Pseudomonas chloroaphis*, it was generally believed to be necessary to supplement with hazardous chemicals, such as acetonitrile, acrylonitrile, acrylamide, and the like. However, enzymatic activity in nitrile hydratase producing microorganisms can be induced with the use of non-hazardous media additives, such as amide containing amino acids and derivates thereof, and optionally stabilized with trehalose. Optionally, asparagine, glutamine, or combinations thereof, can be used as inducers. Methods of inducing and stabilizing enzymatic activity in microorganisms are described in U.S. Pat. Nos. 7,531,343 and 7,531,344, which are incorporated herein by reference.

The disclosed methods of inducing enzymatic activity provide for the production and stability of endotoxin-free asparaginase enzymes using modified media, immobilization, and stabilization techniques, as described herein. For example, enzymatic activity can be induced and stabilized through use of media comprising amide-containing amino acids, or derivatives thereof, and, optionally stabilized by, trehalose. In some embodiments, the methods of induction and stabilization comprise culturing a nitrile hydratase producing microorganism in a medium comprising one or more amide containing amino acids or derivatives thereof, and, optionally, trehalose. Optionally, disclosed are methods for inducing nitrile-hydratase using a medium supplemented with amide containing amino acids or derivatives thereof, which preferably include asparagine, glutamine or a combination thereof. Optionally, disclosed are methods for inducing nitrile-hydratase using a nutritionally complete medium supplemented with only asparagine. Optionally, disclosed are methods for inducing nitrile-hydratase using a nutritionally complete medium supplemented with only glutamine. Optionally, disclosed are methods for stabilizing endotoxin-free asparaginase enzymes using a nutritionally complete medium supplemented with only trehalose. More particularly, the methods of induction and stabilization comprise culturing the microorganism in the medium and optionally collecting the cultured microorganisms or enzymes produced by the microorganisms.

Induction and stabilization of enzymes can be achieved without the use of hazardous nitriles. However, while the induction methods eliminate the need for hazardous chemicals for enzyme activity induction, the use of such further inducers is not excluded. For example, one or more nitriles could be used to assist in specific activity development. Media supplemented with succinonitrile and cobalt can be useful for induction of endotoxin-free asparaginase enzymes. However, the use of nitriles is not necessary for induction of enzyme activity. While the use of nitriles and other hazardous chemicals is certainly not preferred, optionally, such use is possible.

In some embodiments, the endotoxin-free asparaginase enzyme is a recombinant protein. Optionally, host cells that have been genetically engineered to express an endotoxin-free asparaginase enzymes can be produced. Specifically, a polynucleotide that encodes endotoxin-free asparaginase enzymes may be introduced by standard molecular biology techniques into a host cell to produce a transgenic cell that expresses the endotoxin-free asparaginase enzymes. The use of the terms "polynucleotide," "polynucleotide construct," "nucleotide," or "nucleotide construct" is not intended to limit to polynucleotides or nucleotides comprising DNA. Those of ordinary skill in the art will recognize that polynucleotides and nucleotides can comprise ribonucleotides and combinations of ribonucleotides and deoxyribonucleotides. Such deoxyribonucleotides and ribonucleotides include both naturally occurring molecules and synthetic analogues. The polynucleotides described herein encompass all forms of sequences including, but not limited to, single-stranded forms, double-stranded forms, and the like.

Low Mass NHase genes α and β are located in one cassette together and are directly next to each other.

DNA Sequence of Cobalt Containing Low Mass, Nitrile Hydratase Subunit Alpha (EC 4.2.1.84) [Gene nhlA] in *R. rhodochrous* DAP 96253.

(SEQ ID NO: 1)
ATGACCGCCCATAATCCCGTCCAGGGCACGTTGCCACGATCGAACGAG

GAGATCGCCGCACGCGTGAAGGCCATGGAGGCCATCCTCGTCGACAAGGG

CCTGATCTCCACCGACGCCATCGACCACATGTCCTCGGTCTACGAGAACG

AGGTCGGTCCTCAACTCGGCGCCAAGATCGTCGCCCGCGCCTGGGTCGAT

CCCGAGTTCAAGCAGCGCCTGCTCACCGACGCCACCGGCGCCTGCCGTGA

AATGGGCGTCGGCGGCATGCAGGGCGAAGAAATGGTCGTGCTGGAAAACA

CCGACACGGTCCACAACATGGTCGTATGTACCTTGTGCTCGTGCTATCCG

TGGCCGGTTCTCGGCCTGCCACCCAACTGGTACAAGTACCCCGCCTACCG

CGCCCGCGCTGTCCGCGACCCCCGAGGTGTGCTGGCCGAATTCGGATATA

CCCCCGACCCTGACGTCGAGATCCGGATATGGGACTCGAGTGCCGAACTT

CGCTACTGGGTCCTGCCGCAACGCCCAACCGGCACCGAGAACTTCACCGA

AGAACAACTCGCCGACCTCGTCACCCGCGACTCGCTCATCGGCGTATCCG

TCCCCACCACACCTAGCAAGGCCTGA.

Amino Acid Sequence of Cobalt Containing Low Mass, Nitrile Hydratase Subunit Alpha (EC 4.2.1.84) [Encoded by Gene nhlA] in *R. rhodochrous* DAP 96253.

(SEQ ID NO: 2)
MTAHNPVQGTLPRSNEEIAARVKAMEAILVDKGLISTDAIDHMSSVYENE

VGPQLGAKIVARAWVDPEFKQRLLTDATGACREMGVGGMQGEEMVVLENT

DTVHNMVVCTLCSCYPWPVLGLPPNWYKYPAYRARAVRDPRGVLAEFGYT

PDPDVEIRIWDSSAELRYWVLPQRPTGTENFTEEQLADLVTRDSLIGVSV

PTTPSKA.

DNA Sequence of Cobalt Containing Low Mass, Nitrile Hydratase Subunit Beta (EC 4.2.1.84) [Gene nhlB] in *R. rhodochrous* DAP 96253.

(SEQ ID NO: 3)
ATGGATGGAATCCACGACCTCGGTGGCCGCGCCGGCCTGGGTCCGATC

AAGCCCGAATCCGATGAACCTGTTTTCCATTCCGATTGGGAGCGGTCGGT

TTTGACGATGTTCCCGGCGATGGCCCTGGCCGGCGCGTTCAATCTCGACC

```
AGTTCCGGGGCGCGATGGAGCAGATCCCCCCGCACGACTACCTGACCTCG

CAATACTACGAGCACTGGATGCACGCGATGATCCACCACGGCATCGAGGC

GGGCATCTTCGATTCCGACGAACTCGACCGCCGCACCCAGTACTACATGG

ACCATCCGGACGAAACGACCCCCACGCGGCAGGATCCGCAACTGGTGGAG

ACGATCTCGCAACTGATCACCCACGGAGCCGATTACCGACGCCCGACCGA

CACCGAGGCCGCATTCGCCGTAGGCGACAAAGTCATCGTGCGGTCGGACG

CCTCACCGAACACCCACACCCGCCGCGCCGGGTACGTCCGCGGTCGTGTC

GGCGAAGTCGTGGCGACCCACGGCGCGTATGTCTTTCCGGACACCAACGC

ACTCGGCGCCGGCGAAAGCCCCGAACACCTGTACACCGTGCGGTTCTCGG

CGACCGAGTTGTGGGGTGAACCTGCCGCCCCGAACGTCGTCAATCACATC

GACGTGTTCGAACCGTATCTGCTACCGGCCTGA.
```

Amino Sequence of Cobalt Containing Low Mass, Nitrile Hydratase Subunit Beta (EC 4.2.1.84) [Encoded by Gene nhlB] in *R. rhodochrous* DAP 96253.

```
                                          (SEQ ID NO: 4)
MDCIHDLGGRAGLGPIKPESDEPVFHSDWERSVLTMFPAMALAGAFNLDQ

FRGAMEQIPPHDYLTSQYYEHWMHAMIHHGIEAGIFDSDELDRRTQYYMD

HPDETTPTRQDPQLVETISQLITHGADYRRPTDTEAAFAVGDKVIVRSDA

SPNTHTRRAGYVRGRVGEVVATHGAYVFPDTNALGAGESPEHLYTVRFSA

TELWGEPAAPNVVNHIDVFEPYLLPA.
```

High Mass NHase genes α and β are located in a cassette together directly next to each other. That the location of these two NHases are contiguous (i.e., beta and alpha subunits are nest to each other).

DNA Sequence of Cobalt Containing High-Mass, Nitrile Hydratase Subunit Alpha (EC 4.2.1.84) [Gene nhhA] in *R. rhodochrous* DAP 96253.

```
                                          (SEQ ID NO: 5)
GTGAGCGAGCACGTCAATAAGTACACGGAGTACGAGGCACGTACCAAG

GCAATCGAAACCTTGCTGTACGAGCGAGGGCTCATCACGCCCGCCGCGGT

CGACCGAGTCGTTTCGTACTACGAGAACGAGATCGGCCCGATGGGCGGTG

CCAAGGTCGTGGCCAAGTCCTGGGTGGACCCTGAGTACCGCAAGTGGCTC

GAAGAAGACGCGACGGCCGCGATGGCGTCATTGGGCTATGCCGGCGAGCA

GGCACACCAGATCTCGGCCGTCTTCAACGACTCCCAAACACATCACGTAG

TGGTGTGCACTCTGTGTTCGTGCTATCCGTGGCCGGTGCTTGGCCTCCCG

CCCGCCTGGTACAAGAGCATGGAGTACCGGTCCCGAGTGGTAGCAGACCC

TCGTGGAGTACTCAAGCGCGATTTCGGGTTCGACATCCCCGATGAGGTGG

AGGTCAGGGTTTGGGACAGCAGCTCCGAAATCCGCTACATCGTCATCCCG

GAACGGCCGCCGGCACCGACGGTTGGTCCGAGGACGAGCTGGCGAAGCT

GGTGAGTCGGGACTCGATGATCGGTGTCAGTAATGCGCTCACACCGCAGG

AAGTGATCGTATGA.
```

Amino Acid Sequence of Cobalt Containing High-Mass, Nitrile Hydratase Subunit Alpha (EC 4.2.1.84) [Encoded by Gene nhhA] in *R. rhodochrous* DAP 96253.

```
                                          (SEQ ID NO: 6)
VSEHVWVVWDPEYRKWLEEDATAAMASLGYAGEQAHQISAVFNDSQTHHV

VVCTLCSCYPWPVLGLPPAWYKSMEYRSRVVADPRGVLKRDFGFDIPDEV

EVRVWDSSSEIRYIVIPERPAGTDGWSEDELAKLVSRDSMIGVSNALTPQ

EVIV.
```

DNA Sequence of Cobalt Containing High-Mass, Nitrile Hydratase Subunit Beta (EC 4.2.1.84) [Gene nhhB] in *R. rhodochrous* DAP 96253.

```
                                          (SEQ ID NO: 7)
ATGGATGGTATCCACGACACAGGCGGCATGACCGGATACGGACCGGTC

CCCTATCAGAAGGACGAGCCCTTCTTCCACTACGAGTGGGAGGGTCGAAC

CCTGTCGATTCTGACCTGGATGCATCTCAAGGGCATGTCGTGGTGGGACA

AGTCGCGGTTCTTCCGGGAGTCGATGGGGAACGAAAACTACGTCAACGAG

ATTCGCAACTCGTACTACACCCACTGGCTGAGTGCGGCGGAACGTATCCT

CGTCGCCGACAAGATCATCACCGAAGAAGAGCGAAAGCACCGCGTGCAGG

AGATCCTCGAGGGTCGGTACACGGACAGGAACCCGTCGCGGAAGTTCGAT

CCGGCCGAGATCGAGAAGGCGATCGAGAGGCTTCACGAGCCCCACTCCCT

AGTGCTTCCAGGAGCGGAGCCGAGTTTCTCCCTCGGTGACAAGGTCAAAG

TGAAGAACATGAACCCGCTGGGACACACACGGTGCCCGAAGTATGTGCGG

AACAGAATCGGGGAAATCGTCACCTCCCACGGGTGCCAGATCTATCCCGA

GAGCAGCTCCGCCGGCCTCGGCGACGATCCCCGCCCGCTCTACACGGTCG

CGTTTTCCGCCCAGGAACTGTGGGGCGACGACGGAAACGGGAAAGACGTA

GTGTGCGTCGATCTCTGGGAACCGTACCTGATCTCTGCGTGA.
```

Amino Acid Sequence of Cobalt containing High-Mass, Nitrile Hydratase subunit beta (EC 4.2.1.84) [encoded by gene nhhB] in *R. rhodochrous* DAP 96253.

```
                                          (SEQ ID NO: 8)
MDGIHDTGGMTGYGPVPYQKDEPFFHYEWEGRTLSILTWMHLKGMSWWD

KSRFFRESMGNENYVNEIRNSYYTHWLSAAERILVADKIITEEERKHRVQ

EILEGRYTDRNPSRKFDPAEIEKAIERLHEPHSLVLPGAEPSFSLGDKVK

VKNMNPLGHTRCPKYVRNRIGEIVTSHGCQIYPESSSAGLGDDPRPLYTV

AFSAQELWGDDGNGKDVVCVDLWEPYLISA.
```

DNA Sequence of a L-Asparaginase Type-2 Enzyme in *R. rhodochrous* DAP 96253.

```
                                          (SEQ ID NO: 9)
TTGAGCGTCGAACTCGTGGAAGTGGTGCGATCGGGGTTCCGCGAATGC

GTGCACCGCGGCTCGCTCGTCGTACTCGACCCGGCCGGCGACGTGCGGCT

CGCACTGGGCGAGATCCGCACGCCGATCTATCCGCGGTCGTCGAACAAGC

CGCTGCAGGCGGTGGCGCTGCTGCGGCAGGGCTTCGTGCCCCGCTCGACG

GAGGAACTCGCGATCGCGACGGCCTCGCACGAGGGCGAGGCCGGGCACGT

CCGGCTGGTGGAGGCGCTGCTCGCCGGGCACGGATTCACCGAGGACGACC

TGCAGTGCCCGCCGGATCTGCCGGGCAACGAACCGGCCCGGGCGACGATC
```

```
GTCGCCGCCGGTCACCCCCGGCGGACGGTGTACATGAACTGCTCCGGCAA

GCACGCCGCGATGCTCGCGACGTGCGCCGCGAACGGCTGGCCCGTCCGCG

CCGGCGCGGACGAGCCGGGCTACCTCGACTCCGCCCATCCGCTGCAGCAG

GCCGTGGTCGAGACGGTCCTCGACCTCGCGGGCGACGTCGAGGACACCGA

TCTCGGCATCGACGGGTGCGGCCTGCCGATCGTGCCGCTGCCCCTGGTCA

ATCTCGCCCGGGCCTATTCGCGGCTGGCGACGGCCGGGCCCGGGACGCCG

GAACGGGCCGTGGCCGACGCGATCCGGAGTCATCCGCACCTCGTCTCGGG

CACCGGCAAGGACGACGCCCGGTTGATGCCCGCGGTGCCGGGACTGCTGT

GCAAGGCCGGGGCGGACGGCGTGCACGCGGGTGCCCTGCCGGACGGCACC

GCGTTCGCACTGAAGATCGACGACGGCCACGAGCGGGCCCGCCTTCCCCT

CACTGCCGCCCTGCTGCACCACCTCGGAGTGACGTGGTCCGAGGAGCACG

CGGAGCTCGCGTCGCAGCCGGTGCTCGGCGGTGGGATCCGGGTCGGCACG

GTCCGGGCGATCCCCGGAGTGCTCTGA.
```

Amino Acid Sequence of a L-Asparaginase Type-2 Enzyme in *R. rhodochrous* DAP 96253.

```
                                           (SEQ ID NO: 10)
LSVELVEVVRSGFRECVHRGSLVVLDPAGDVRLALGEIRTPIYPRSSNKP

LQAVALLRQGFVPRSTEELAIATASHEGEAGHVRLVEALLAGHGFTEDDL

QCPPPDLPGNEPARATIVAAGHPRRTVYMNCSGKHAAMLATCAANGWPVRA

GADEPGYLDSAHPLQQAVVETVLDLAGDVEDTDLGIDGCGLPIVPLPLVN

LARAYSRLATAGPGTPERAVADAIRSHPHLVSGTGKDDARLMPAVPGLLC

KAGADGVHAGALPDGTAFALKIDDGHERARLPLTAALLHHLGVTWSEEHA

ELASQPVLGGGIRVGTVRAIPGVL.
```

DNA Sequence of an Amidase which is Clustered with an UREA ABC Transporter and Nitrile Hydratase in *R. rhodochrous* DAP 96253.

```
                                           (SEQ ID NO: 11)
ATGTCTTCGTTGACTCCCCCCAATTCCAACCAAATGTCGGCCCTGAACAA

CCACTTCCGATTCGGACTGACGACGCCGGAACTCGAAGAGTTCGCACCGG

CCCTCGAAGCGACGCTCGCGTCCTCCGAAACCGTCGAACGCCTCTACGAG

CGCACCGCGCCCGAGCCGCCTCAGCGGTCATGGACCTCACCCACGGCGGA

CGAGAACCCGCTGAGCGCCTGGTACGTCACCACCTCGATCAGCGAAACCG

ACGAAGGCCCCCTCGCCGGGCGAACGGTCGCCGTGAAAGACAACGTCGCA

GTCGCCGGCGTGCCGATGATGAACGGCTCCCGAACCGTCGAGGGCTTCAC

CCCCCGCTACGACGCCACCGTCGTACGCCGACTGCTCGACGCCGGCGCAA

CCATCACCGGCAAAGCGGTGTGCGAAGATCTCTGCTTCTCCGGCGCCAGC

TTCACTTCCCACCCCCAGCCGGTCCGCAACCCCTGGGACGAAAGCCGCAT

CACCGGCGGCTCGTCCAGCGGCAGCGGCGCCCTGGTCGCCAGCGGCCAGG

TGGATATGGCAGTCGGCGGCGACCAGGGCGGTTCGATCCGCATCCCCGCC

GCGTTCTGCGGCATCGTCGGACACAAACCCACCCACGGACTGGTCCCCTA

TACGGGAGCATTTCCCATCGAACGAACCATCGACCACCTCGGTCCGATGA

CGCGCACGGTCAGCGACGCCGCCGCAATGCTCACCGTCCTCGCCGGCACC

GACGGCCTCGATCCCCGACAGACCCACCGGATCGAACCGGTGGACTACCT

CGCGGCGCTGGCCGAACCCGCATCGGGTCTGCGCGTGGGTGTGGTCACCG

AAGGCTTCGACACCCCTGTCTCCGACGCTGCCGTCGACAATGCCGTGCGC

ACCGCCATCGGCGTACTGCGCTCGGCCGGACTTACCGTCGAAGAGGTCTC

GATCCCCTGGCACCTCGATGCGATGGCCGTCTGGAACGTGATCGCCACCG

AGGGAGCGGCCTACCAGATGCTCGACGGCAATGCCTACGGCATGAACACT

GATGGCTTCTACGATCCCGAACTGATCGCCCACTTCTCCCGTCAACGACT

CGAGCACGGTCACCAACTGTCGAAGACGGTCAAACTCGTCGGGATGTCCG

GGCGCTACACATTGGAGGTAGGCGGCGGCAAGTACTACGCCATGGCCCGC

CAACTCGTCCCCGAAGTCCGCGCCGCCTACGACGCCGCCTTGGCTCGGTA

CGACGTGCTGGTGATGCCCACCCTCCCCTACACCGCCACCAAGATCCCGA

CCACGGACATTCCGTTGGCCGACTATCTGGACACCGCACTGTCGATGATC

ATCAACACCGCACCATTCGACGTCACCGGTCACCCCGCCTGCAGTGTCCC

CGCTGACCTGGTCCACGGGCTTCCCACCGGAATGATGATCATCGGCAAGC

ATTTCGACGACGCGACAGTGCTGCGCGTCGCCCAGCTCTACGAACATGCA

GTGGGCAACTATCCTGTCCCGCCGGCTGCAGCCGGCACCCTGACATAA.
```

Amino Acid Sequence of an Amidase which is Clustered with an UREA ABC Transporter and Nitrile Hydratase in *R. rhodochrous* DAP 96253.

```
                                           (SEQ ID NO: 12)
MSSLTPPNSNQMSALNNHFRFGLTTPELEEFAPALEATLASSETVERLYE

RTAPEPPQRSWTSPTADENPLSAWYVTTSISETDEGPLAGRTVAVKDNVA

VAGVPMMNGSRTVEGFTPRYDATVVRRLLDAGATITGKAVCEDLCFSGAS

FTSHPQPVRNPWDESRITGGSSSGSGALVASGQVDMAVGGDQGGSIRIPA

AFCGIVGHKPTHGLVPYTGAFPIERTIDHLGPMTRTVSDAAAMLTVLAGT

DGLDPRQTHRIEPVDYLAALAEPASGLRVGVVTEGFDTPVSDAAVDNAVR

TAIGVLRSAGLTVEEVSIPWHLDAMAVWNVIATEGAAYQMeDGNAYGMNT

DGFYDPELIAHFSRQRLEHGHQLSKTVKLVGMSGRYTLEVGGGKYYAMAR

QLVPEVRAAYDAALARYDVLVMPTLPYTATKIPTTDIPLADYLDTALSMI

INTAPFDVTGHPACSVPADLVHGLPTGMMIIGKHFDDATVLRVAQLYEHA

VGNYPVPPAAAGTLT.
```

Variants and fragments of polynucleotides that encode polypeptides that retain the desired asparaginase activity may also be used herein. By "fragment" is intended a portion of the polynucleotide and hence also encodes a portion of the corresponding protein. Polynucleotides that are fragments of an enzyme nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length enzyme polynucleotide sequence. A polynucleotide fragment will encode a polypeptide with a desired enzymatic activity and will generally encode at least 15, 25, 30, 50, 100, 150, 200, or 250 contiguous amino acids, or up to the total number of amino acids present in a full-length enzyme amino acid sequence. "Variant" is intended to mean substantially similar sequences. Generally, variants of a particular enzyme sequence will have at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the reference enzyme sequence, as determined by standard sequence alignment programs. Variant polynucleotides described herein will encode polypeptides with the desired enzyme activity. By way of example, the relatedness between two polynucleotides or two polypeptides can be described as identity. The identity between two sequences can be determined using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, Trends Genet. 16:276-7). The output of Needle labeled "longest identity" is used as the percent identity and is calculated as (Identical Residues (i.e., nucleotides or peptides)×100)/(Length of Alignment−Total Number of Gaps in Alignment).

As used in the context of production of transgenic cells, the term "introducing" is intended to mean presenting to a host cell, such as *Escherichia coli*, with a polynucleotide that encodes an endotoxin-free asparaginase enzyme.

Optionally, the polynucleotide will be presented in such a manner that the sequence gains access to the interior of a host cell, including its potential insertion into the genome of the host cell. The disclosed methods do not depend on a particular protocol for introducing a sequence into a host cell, only that the polynucleotide gains access to the interior of at least one host cell. Methods for introducing polynucleotides into host cells are well known, including, but not limited to, stable transfection methods, transient transfection methods, and virus-mediated methods. "Stable transfection" is intended to mean that the polynucleotide construct introduced into a host cell integrates into the genome of the host and is capable of being inherited by the progeny thereof. "Transient transfection" or "transient expression" is intended to mean that a polynucleotide is introduced into the host cell but does not integrate into the host's genome.

Furthermore, the endotoxin-free asparaginase enzyme sequence may be contained in, for example, a plasmid for introduction into the host cell. Typical plasmids of interest include vectors having defined cloning sites, origins of replication, and selectable markers. The plasmid may further include transcription and translation initiation sequences and transcription and translation terminators. Plasmids can also include generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or optimally both. For general descriptions of cloning, packaging, and expression systems and methods, see Giliman and Smith, Gene 8:81-97 (1979); Roberts et al., Nature 328:731-734 (1987); Berger and Kimmel, Guide to Molecular Cloning Techniques, Methods in Enzymology, Vol. 152 (Academic Press, Inc., San Diego, Calif.) (1989); Sambrook et al., Molecular Cloning: A Laboratory Manual, Vols. 1-3 (2d ed; Cold Spring Harbor Laboratory Press, Plainview, N.Y.) (1989); and Ausubel et al., Current Protocols in Molecular Biology, Current Protocols (Greene Publishing Associates, Inc., and John Wiley & Sons, Inc., New York; 1994 Supplement) (1994). Transgenic host cells that express endotoxin-free asparaginase enzyme may be used in the disclosed methods as whole cells or as a biological source from which one or more enzymes can be isolated.

In some embodiments, the disclosed endotoxin-free asparaginase enzyme is a heteropolymer containing at least one polypeptide having an amino acid sequence with at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:2, 4, 6, 8, or 10. A person skilled in the art will understand how to select and design variant proteins retaining substantially their L-asparaginase activity. Typically, a Nessler assay is used for the determination of L-asparaginase activity according to a method described by Mashburn and Wriston (Mashburn, L., and Wriston, J. (1963) "Tumor Inhibitory Effect of L-Asparaginase," Biochem Biophys Res Commun 12, 50, incorporated herein by reference in its entirety).

Endotoxin-free asparaginase enzyme may be produced constitutively in a cell or, alternatively, a cell may produce the endotoxin-free asparaginase enzyme only following "induction" with a suitable inducing agent. "Constitutively" is intended to mean that at least one enzyme disclosed herein is continually produced or expressed in a particular cell type. Other cell types, however, may need to be "induced," as described above, to express endotoxin-free asparaginase enzyme at a sufficient quantity or enzymatic activity level to cell growth. That is, endotoxin-free asparaginase enzyme may only be produced (or produced at sufficient levels) following exposure to or treatment with a suitable inducing agent. Such inducing agents are known and outlined above. For example, the one or more bacteria are treated with an inducing agent such as urea, methyl carbamate, cobalt, asparagine, glutamine, or any mixture thereof, more particularly urea or methyl carbamate optionally in combination with asparagine or cobalt. Furthermore, as disclosed in U.S. Pat. Nos. 7,531,343 and 7,531,344, which are incorporated by reference in their entireties, asparaginase activity can be induced in *Rhodococcus rhodochrous* DAP 96622 (Gram-positive) or *Rhodococcus rhodochrous* DAP 96253 (Gram-positive), in medium supplemented with amide containing amino acids or derivatives thereof. Other strains of *Rhodococcus* can also preferentially be induced to exhibit asparaginase enzymatic activity utilizing amide containing amino acids or derivatives thereof.

Polymers to Stabilize Asparaginase

The disclosed endotoxin-free asparaginase enzymes may be stored under conditions suitable to preserve enzymatic activity. In some embodiments, the disclosed endotoxin-free asparaginase enzyme is conjugated to a polymer in order to increase its stability. Suitable polymers can be selected from the group of non-toxic water soluble polymers such as polysaccharides, e.g. hydroxyethyl starch, poly amino acids, e.g. poly lysine, polyester, e.g., polylactic acid, and poly alkylene oxides, e.g., polyethylene glycol (PEG).

Polyethylene glycol (PEG) or mono-methoxy-polyethyleneglycol (mPEG) is well known in the art and comprises linear and branched polymers. Examples of some polymers, particularly PEG, are provided in the following, each of which is herein incorporated by reference in its entirety: U.S. Pat. Nos. 5,672,662; 4,179,337; 5,252,714; US Pat. Appl. Publ. No. 2003/0114647; U.S. Pat. Nos. 6,113,906; 7,419,600; and PCT Publ. No. WO2004/083258.

The quality of such polymers is characterized by the polydispersity index (PDI). The PDI reflects the distribution of molecular weights in a given polymer sample and is calculated from the weight average molecular weight divided by the number average molecular weight. It indicates the distribution of individual molecular weights in a batch of polymers. The PDI has a value always greater than 1, but as the polymer chains approach the ideal Gauss distribution monodispersity), the PDI approaches 1.

The polyethylene glycol has advantageously a molecular weight comprised within the range of about 500 Da to about 9,000 Da. More specifically, the polyethylene glycol (e.g, mPEG) has a molecular weight selected from the group consisting of polyethylene glycols of 2000 Da, 2500 Da, 3000 Da, 3500 Da, 4000 Da, 4500 Da, and 5000 Da. In a particular embodiment, the polyethylene glycol (e.g., mPEG) has a molecular weight of 5000 Da.

The number of PEG moieties which can be coupled to the enzyme will be subject to the number of free amino groups and, even more so, to which amino groups are accessible for a PEGylation reaction. In a particular embodiment, the degree of PEGylation (i.e., the number of PEG moieties coupled to amino groups on the NHase-asparaginase) is within a range from about 10% to about 100% of free and/or accessible amino groups (e.g., about 10%, 15%, 20%, 25%, 30%, 40%, 50%, 60%, 70%, 80%, 90%, or 100%). 100% PEGylation of accessible amino groups (e.g., lysine residues and/or the N-terminus of the protein) is also referred to herein as "maximally PEGylated." One method to determine the modified amino groups in mPEG-r-crisantaspase conjugates (degree of PEGylation) is a method described by Habeeb (A.F.S.A. Habeeb, "Determination of free amino groups in proteins by trinitrobenzensulfonic acid", Anal. Biochem. 14 (1966), p. 328, incorporated herein by reference in its entirety).

In one embodiment, the PEG moieties are coupled to one or more amino groups (wherein amino groups include lysine residues and/or the N-terminus) of the NHase-asparaginase. In a particular embodiment, the degree of PEGylation is within a range of from about 10% to about 100% of total or accessible amino groups (e.g., lysine residues and/or the N-terminus), e.g., about 10%, 15%, 20%, 25%, 30%, 35%, 40%, 45%, 50%, 55%, 60%, 65%, 70%, 75%, 80%, 85%, 90%, 95% or 100%. In a specific embodiment, about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% of the total amino groups (e.g., lysine residues and/or the N-terminus) are coupled to a PEG moiety. In another specific embodiment, about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the accessible amino groups (e.g., lysine residues and/or the N-terminus) are coupled to a PEG moiety. In a specific embodiment, 40-55% or 100% of the accessible amino groups (e.g., lysine residues and/or the N-terminus) are coupled to a PEG moiety. In some embodiments, the PEG moieties are coupled to the NHase-asparaginase by a covalent linkage.

Treating Diseases Treatable by L-Asparagine Depletion

The disclosed endotoxin-free asparaginase enzyme can be used in the treatment of a disease treatable by depletion of asparagine. For example, the disclosed endotoxin-free asparaginase enzyme is useful in the treatment or the manufacture of a medicament for use in the treatment of acute lymphoblastic leukemia (ALL) in both adults and children, as well as other conditions where asparagine depletion is expected to have a useful effect. Such conditions include, but are not limited to the following: malignancies, or cancers, including but not limited to hematalogic malignancies, non-Hodgkin's lymphoma, NK lymphoma, pancreatic cancer, Hodgkin's disease, acute myelocytic leukemia, acute myelomonocytic leukemia, chronic lymphocytic leukemia, lymphosarcoma, reticulosarcoma, and melanosarcoma. Representative non-malignant hematologic diseases which respond to asparagine depletion include immune system-mediated blood diseases, e.g., infectious diseases such as those caused by HIV infection (i.e., AIDS). Non-hematologic diseases associated with asparagine dependence include autoimmune diseases, for example rheumatoid arthritis, SLE, autoimmune, collagen vascular diseases, AIDS, etc. Other autoimmune diseases include osteo-arthritis, Issac's syndrome, psoriasis, insulin dependent diabetes mellitus, multiple sclerosis, sclerosing panencephalitis, systemic lupus erythematosus, rheumatic fever, inflammatory bowel disease (e.g., ulcerative colitis and Crohn's disease), primary billiary cirrhosis, chronic active hepatitis, glomerulonephritis, myasthenia gravis, pemphigus vulgaris, and Graves' disease. Cells suspected of causing disease can be tested for asparagine dependence in any suitable in vitro or in vivo assay, e.g., an in vitro assay wherein the growth medium lacks asparagine.=

In some embodiments, endotoxin-free asparaginase enzyme is administered as a first line therapy. In another embodiment, endotoxin-free asparaginase enzyme is administered as a second line therapy in patients, particularly patients with ALL, where objective signs of hypersensitivity have developed to other asparaginase preparations. Non-limiting examples of objective signs of hypersensitivity include testing "antibody positive" for an asparaginase enzyme In some embodiments, the disclosed method involves administering to a patient in need of the treatment a therapeutically effective amount of a disclosed endotoxin-free asparaginase enzyme. In a specific embodiment, treatment will be administered as part of a combination of chemotherapy drugs, including, but not limited to glucocorticoids, corticosteroids, anticancer compounds or other agents, including, but not limited to methotrexate, dexamethasone, prednisone, prednisolone, vincristine, cyclophosphamide, and anthracycline. In some embodiments, patients with ALL will be administered the endotoxin-free asparaginase enzyme as a component of multi-agent chemotherapy during three chemotherapy phases including induction, consolidation or intensification, and maintenance. The endotoxin-free asparaginase enzyme can be administered before, after, or simultaneously with other compounds as part of a multi-agent chemotherapy regimen.

In some embodiments, the method comprises administering endotoxin-free asparaginase enzyme at an amount of about 1 U/kg to about 25 U/kg (e.g., about 1, 2, 3, 4, 5, 6, 7, 8, 9, 10, 11, 12, 13, 14, 15, 16, 17, 18, 19, 20, 21, 22, 23, 24, or 25 U/kg) or an equivalent amount thereof (e.g., on a protein content basis). In some embodiments, the endotoxin-free asparaginase enzyme is administered at a dose that depletes L-asparagine to undetectable levels using methods and apparatus known in the art for a period of about 3 days to about 10 days (e.g., 3, 4, 5, 6, 7, 8, 9, or 10 days) for a single dose.

The incidence of relapse in ALL patients following treatment with existing L-asparaginase remains high, with approximately 10-25% of pediatric ALL patients having early relapse (e.g., some during maintenance phase at 30-36 months post-induction). If a patient treated with *E. coli*-derived L-asparaginase has a relapse, subsequent treatment with *E. coli* preparations could lead to a "vaccination" effect, whereby the *E. coli* preparation has increased immunogenicity during the subsequent administrations. In one embodiment, the disclosed endotoxin-free asparaginase enzyme may be used in a method of treating patients with relapsed ALL who were previously treated with other asparaginase preparations, in particular those who were previously treated with *E. coli*-derived asparaginases.

Compositions, Formulations, and Routes of Administration

Also disclosed is a pharmaceutical composition comprising a disclosed endotoxin-free asparaginase enzyme in a pharmaceutically acceptable carrier.

Pharmaceutical compositions containing the disclosed endotoxin-free asparaginase enzyme can be administered to a patient using standard techniques. Techniques and formulations generally may be found in Remington's Pharmaceutical Sciences, 18th ed., Mack Publishing Co., Easton, Pa., 1990 (herein incorporated by reference).

Suitable dosage forms, in part, depend upon the use or the route of entry, for example, oral, transdermal, transmucosal, or by injection (parenteral). Such dosage forms should allow the therapeutic agent to reach a target cell or otherwise have the desired therapeutic effect. For example, pharmaceutical compositions injected into the blood stream preferably are soluble.

The disclosed conjugates and/or pharmaceutical compositions can be formulated as pharmaceutically acceptable salts and complexes thereof. Pharmaceutically acceptable salts are non-toxic salts present in the amounts and concentrations at which they are administered. The preparation of such salts can facilitate pharmaceutical use by altering the physical characteristics of the compound without preventing it from exerting its physiological effect. Useful alterations in physical properties include lowering the melting point to facilitate transmucosal administration and increasing solubility to facilitate administering higher concentrations of the drug. The pharmaceutically acceptable salt of an asparaginase may be present as a complex, as those in the art will appreciate.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate, and quinate. Pharmaceutically acceptable salts can be obtained from acids, including hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, supra. Such salts can be prepared using the appropriate corresponding bases.

Pharmaceutically acceptable carriers and/or excipients can also be incorporated into a pharmaceutical composition according to the invention to facilitate administration of the particular asparaginase. Examples of carriers suitable for use in the practice of the invention include calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include sterile solutions of water for injection (WFI), saline solution and dextrose.

Pharmaceutical compositions can be administered by different routes, including intravenous, intraperitoneal, subcutaneous, intramuscular, oral, topical (transdermal), or transmucosal administration. For oral administration, for example, the compounds can be formulated into conventional oral dosage forms such as capsules, tablets, and liquid preparations such as syrups, elixirs, and concentrated drops. For injection, pharmaceutical compositions are formulated in liquid solutions, preferably in physiologically compatible buffers or solutions, such as saline solution, Hank's solution, or Ringer's solution.

In addition, the compounds may be formulated in solid form and redissolved or suspended immediately prior to use. For example, lyophilized forms of the conjugate can be produced. In a specific embodiment, the conjugate is administered intramuscularly. In another specific embodiment, the conjugate is administered intravenously. In some embodiments the pharmaceutical composition is contained in a vial as a lyophilized powder to be reconstituted with a solvent.

Systemic administration can also be accomplished by transmucosal or transdermal means. For transmucosal or transdermal administration, penetrants appropriate to the barrier to be permeated are used in the formulation. Such penetrants are well known in the art, and include, for example, for transmucosal administration, bile salts, and fusidic acid derivatives. In addition, detergents may be used to facilitate permeation. Transmucosal administration, for example, may be through nasal sprays, inhalers (for pulmonary delivery), rectal suppositories, or vaginal suppositories. For topical administration, compounds can be formulated into ointments, salves, gels, or creams, as is well known in the art.

The amounts of the composition to be delivered will depend on many factors, for example, the $IC_{50}$, $EC_{50}$, the biological half-life of the compound, the age, size, weight, and physical condition of the patient, and the disease or disorder to be treated. The importance of these and other factors to be considered are well known to those of ordinary skill in the art. Generally, the amount of the composition to be administered will range from about 10 International Units per square meter of the surface area of the patient's body (IU/m2) to 50,000 IU/m2, with a dosage range of about 1,000 IU/m2 to about 15,000 IU/m2 being preferred, and a range of about 6,000 IU/m2 to about 15,000 IU/m2 being more preferred, and a range of about 10,000 to about 15,000 IU/m2 (about 20-30 mg protein/m) being particularly preferred to treat a malignant hematologic disease, e.g., leukemia. Typically, these dosages are administered via intramuscular or intravenous injection at an interval of about 3 times weekly to about once per month, typically once per week or once every other week during the course of therapy. Of course, other dosages and/or treatment regimens may be employed, as determined by the attending physician.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Comparative Analysis of the Sequence Data

The Asparaginase currently used in the treatment of juvenile ALL is a homo-dimer (where two homo-dimers are in intimate association) and its origin is either from *E. coli* or *Erwinia*. Some of the current preparations are recombinant. Like all sub-unit proteins, when introduced into the human body, this protein will break down and be cleared in the urine. Asparagine preparations from *Erwinia* typically clear within 48 hours of administration. The asparagine used is either as is or linked to PEG (polyethylene glycol) [referred to as PEGylated Asparaginase]. PEG-asparaginase takes much longer to clear than *Erwinia* asparaginase. Also note that recombinant proteins produced in Gram-negative hosts typically show enhanced levels of endotoxin when the cells are over-induced or when high-cell density fermentation is attempted.

As disclosed herein, NHase from induced cells of *R. rhodochrous* DAP 96253, has asparaginase activity. The presence of asparaginase activity and the enzyme asparaginase is well documented in Gram-negative bacteria, and especially in *Escherichia coli* and in *Erwinia* spp. In both *E. coli* and in *Erwinia*, active asparaginase is a homo-dimer (actually the association is to form two intimate homo-dimers). In induced cells of *R. rhodochrous* DAP 96253, the isolated and purified active NHase (which exhibits asparaginase activity in addition to NHase activity) is composed of >8 α-subunits and >8 β-subunits (>16 merup to 20 mer). In this NHase, the α- and β-subunits are essentially in parity (i.e., 1:1 ratio). Furthermore this enzyme contains non-corrin-Cobalt at the active site. Thus the secondary, tertiary and quaternary structure of the classic asparaginase seen in Gram-negative bacteria the "NHase-asparaginase" in induced cells of *R. rhodochrous* DAP 96253 are very different.

Sequencing of the α- and β-subunits of the isolated and highly purified NHase from induced cells of *R. rhodochrous* DAP 96253 show that the sequence of these subunits is unlike the sequence(s) seen in asparaginases obtained from other bacteria (i.e. Gram-negative or Gram-positive). Thus the primary structure (amino acid sequence) of *R. rhodochrous* DAP 96253 NHase, exhibiting asparaginase activity is unique as well.

Recent literature shows the presence of asparaginase enzymes in selected members of the Mycolata (*Norcardia, Mycobacterium*, and *Rhodococcus*). However, while analysis of these asparaginase enzymes from the Mycolata show some commonality with the asparaginase enzymes seen in Gram-negative bacteria, these asparaginase enzymes from the Mycolata (and from *Rhodococcus* spp. are not similar to the purified NHase of induced cells of *R. rhodochrous* DAP 96253 which exhibits asparaginase activity.

During induction of *R. rhodochrous* DAP 96253 during fermentation, the high levels of NHase>150 units/mg-cell dry weight (typically 200-600 units of NHase), also show higher levels of asparaginase 20-30 units/mg-cell dry weight than the levels of asparaginase seen in *E. coli* or *Erwinia*. When it is considered, that >50 grams of cells per liter is obtained, which is considerably higher than that seen in *E. coli* or *Erwinia*, the amount of asparaginase activity produced per liter is order of magnitudes higher in *R. rhodochrous* DAP 96253. Also the NHase-Asparaginase from *R. rhodochrous* DAP 96253 when purified contains no endotoxin, whereas all preparations of asparaginase from *E. coli* and *Erwinia* contain endotoxin.

"Classic" asparaginase enzymes are homo-dimers arranged as 2-intimate homodimersand that NHase is a hetero-polymer (heterotetramer [low mass] up to hetero20mer [high mass]. It also is important to note that *R. rhodochrous* DAP 96253 has two cobalt containing —NHase enzymes, typically defined as low mass (a heterotetramer) [L-CoNHase], and high-mass (>16-heteromer) [H-CoNHase].

In the past, it has been shown that when induced cells of *R. rhodochrous* DAP 96253 are immobilized in polyacrylamide, the concentration of residual monomer (typically >600 ppm) is rapidly reduced to ppb levels.

Figure 2:
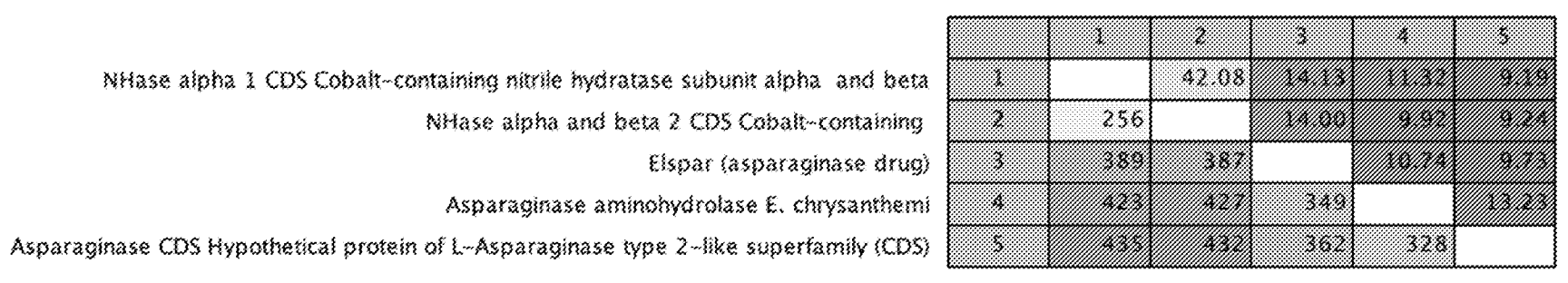

*E. coli* asparaginase (Elspar®) is currently used in veterinary medicine for the treatment of certain leukemias (and related cancers) in animals. In FIG. 2, the amino acid sequences for the subunits of the two NHase-Asparaginase enzymes are compared with each other and also with the classic asparaginase of *R. rhodochrous* DAP 96253, and in addition with the known sequence for the asparaginase pharmaceutical product Elsvar® and with the published asparaginase sequence of *Erwinia chrysanthemi*.

FIG. 2 summarizes the comparative analyses showing percent identity and number of differences. It is clear from the comparative analysis that at best the α-subunit and β-subunit of NHase-Asparaginase share a 14% similarity with *E. chrysanthemi* asparaginase and 10.7% similarity with the Elsvar® asparaginase (*E. coli* derived.) The DNA and protein sequences of the NHase of *R. rhodochrous* DAP 96253 are totally unlike either *E. coli* or *Erwinia chrysanthemi* asparaginase. Thus DNA-sequence/protein sequence of *E. coli* and/or *Erwinia chrysanthemi* asparaginase could not be indicative or predictive of the *R. rhodochrous* DAP 96253 NHase which exhibits asparaginase activity.

A comparison of the NHase subunits show that there is significant homology between the High-Mass NHase subunits of *R. rhodochrous* DAP 96253 and *R. rhodochrous* J1. In essence, the homology is about 98% and the sub-units vary by several amino acids.

On an organizational level, the high-mass NHase operon of strain DAP 96253 contains no IS (insertion sequence), whereas strain J1 contains the gene nnhF which is an Insertion sequence (IS 1164). In addition, preliminary genomic information suggests that the organization of Low-Mass NHase in strain DAP 96253 is dissimilar from Low-Mass NHase organization in strain J1. In J1, both the amidase gene and the Cobalt transporter gene are associated with the Low-Mass NHase operon.

Example 2: Enzyme Preparations Obtained from Cells of *Rhodococcus rhodochrous* DAP 96253 that Possess Different Levels of Asparaginase and/or Glutaminase Amidase Activities Cells of *R. rhodochrous* DAP 96253 are capable of producing nitrile hydratase. When fully-induced (when for example when grown on YEMEA supplemented with cobalt and urea), the cells of *R. rhodochrous* DAP 96253 are capable of producing a high-mass, cobalt containing NHase that exhibits activity against nitriles such as acrylonitrile and acetonitrile. Furthermore, under such conditions the induced Nitrile Hydratase can comprise in excess of 50% of the total soluble protein. The high mass NHase can when purified also be stabilized such that the high-mass NHase activity can be retained for longer periods of time. NHase activity can also be stabilized in whole cells. The overall NHase activity is thus influenced by the amount of NHase produced by the cell and by the ability to stabilize the NHase made by the cells.

When induced for NHase, *R. rhodochrous* DAP 96253 (and also *R. rhodochrous* DAP 96622) also are induced for amidase activity. Furthermore, it was determined that the purified NHase (from induced cells) also exhibited amidase activity (specifically activity against asparagine and glutamine.)

Asparaginase adversely affects cells that are not capable of producing their own asparagine by converting free asparagine to aspartic acid thus stressing those cells incapable of making their own asparagine. Under certain situations of asparagine depletion, it is possible to obtain asparagine by the conversion of glutamine (by for example glutamine synthase or via transamination). The presence of glutaminase, however, will convert glutamine to glutamic acid making the conversion of glutamine to asparagine not possible. The presence of glutaminase along with asparaginase will heighten/intensify the depletion of asparagine.

Asparaginase, obtained from E. coli, has been used since the late 1960s, and subsequently from Erwinia, in the treatment of juvenile ALL (Acute Lymphoblastic Leukemia). The goal of these asparaginase preparations was to have essentially only asparaginase activity and no glutaminase activity. It was thought that the presence of glutaminase activity affected patient sensitivity and resulted in antibody formation. Patients receiving E. coli asparaginase did become sensitized and did develop anti-E. coli asparaginase antibodies limiting effective treatment. Erwinia asparaginase while similar to E. coli asparaginase is not identical, and as such patients who became sensitized to E. coli asparaginase could receive Erwinia asparaginase.

However, both E. coli and Erwinia are Gram-negative bacteria, and therefore produce and contain Endotoxin, and all proteins isolated and purified must be specifically, and rigorously treated to remove Endotoxin. Recently, research has shown that any level of Endotoxin is immunogenic.

In addition, the asparaginase preparation obtained from E. coli or Erwinia are extremely labile, once reconstituted, and must be used within 8 hours of reconstitution. Pegylation was developed so that more stable asparaginase formulations could be made. While PEGylated asparaginase (PEG-ASNase) is considerably more stable than ASNase, it noted that patients who had previously been administered ASNase, quickly responded to the PEG-ASNase, with the PEG-ASNase becoming inactivated by the anti-ASNase antibodies.

NHase purified from induced cells of R. rhodochrous DAP 96253 possesses both asparaginase and glutaminase activity. Recent research suggests that resistance to Asparaginase treatment can be effected by the induction of glutaminase synthase activity by cancer cells, which results in the conversion of glutamine to asparagine, and in not achieving asparagine depletion. The presence of glutaminase with asparaginase provides for a product which will effectively reduce asparagine in Leukemia cells, and also in resistant Leukemia cells capable of producing glutamine synthase.

R. rhodochrous DAP 96253 is a Gram-positive actinomycete, and as such produces no endotoxin. The sequence for R. rhodochrous NHase and amidases are different from the amidases/asparaginases of either E. coli and/or Erwinia.

Figure 5:
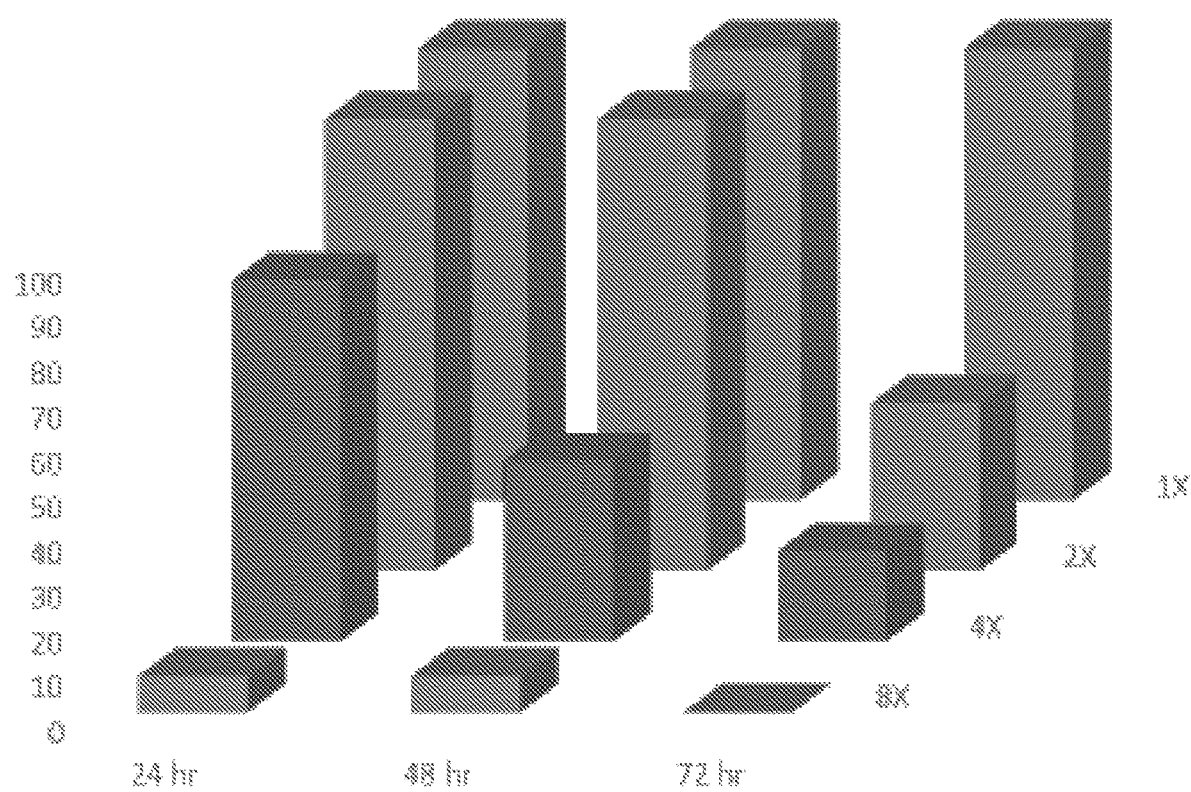
FIG. 5 is a graph showing dose/time response (1×, 2×, 4×, or 8×) of JURKAT (leukemia cells) to purified asparaginase from *R. rhodochrous* DAP 96253 (% JURKAT cells surviving).

FIG. 5 shows the potent activity of the R. rhodochrous purified NHase/amidase [asparaginase/glutaminase] against Jurkat (Leukemia) cells. The procedure used to prepare the Asparaginase/Glutaminase to purity was the same purification scheme employed to prepare and purify high-mass NHase.

In addition, immobilization by calcium alginate, acrylamide/polyacrylamide, calcium alginate Polyethylenimide PEI), and glutaraldehyde-PEI results in very to significant improvements in NHase stability and half-life. Reduced temperature, or increased temperature (with or without acidic conditions) modulate amidase activity resulting in preparations with significant differences in amidase activity and stability.

The preparations prepared from R. rhodochrous DAP 96253 address all of the current concerns with asparaginase products from E. coli and/or Erwinia: 1) it is totally Endotoxin free; 2) it has a unique sequence that will be unreactive with either anti-E. coli ASNase antibodies, or anti-Erwinia ASNase antibodies (PEGylated or non-PEGylated); 3) it addresses ASNase resistance by having glutaminase activity; and 4) it achieves desired asparagine depletion.

The R. rhodochrous DAP 96253 product(s) also has potential for treating other ALLs (Adolescent Young Adult [AYA] and adult), and also for other cancers (e.g. cervical) where asparagine depletion would be advantageous.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject with a disease treatable by L-asparagine depletion, comprising administering to the subject a composition comprising an endotoxin-free asparaginase isolated from *Rhodococcus rhodochrous* DAP 96253 cells, wherein the asparaginase comprises a heteropolymer of a polypeptide having the amino acid sequence as set forth in SEQ ID NO:6 and a polypeptide having the amino acid sequence as set forth in SEQ ID NO:8, wherein the disease is selected from the group consisting of Acute Lymphoblastic Leukemia ("ALL"), acute myelocytic leukemia, acute myelomonocytic leukemia, chronic lymphocytic leukemia, non-Hodgkin's lymphoma, NK lymphoma, and pancreatic cancer.

2. The method of claim 1, wherein the asparaginase is a recombinant asparaginase.

3. The method of claim 1, wherein the cells have been induced to produce the asparaginase using an inducing agent selected from the group consisting of urea, methyl carbamate, methacrylamide, acetamide, cobalt, or asparagine, and combinations thereof.

4. The method of claim 1, wherein the asparaginase is conjugated to a polyethylene glycol (PEG).

5. The method of claim 1, wherein the disease is juvenile or adult ALL.

6. The method of claim 1, wherein the subject has had a previous hypersensitivity to an *Escherichia* L asparaginase or *Erwinia* L-asparaginase.

7. The method of claim 1, wherein the asparaginase is administered in a dose that depletes L-asparagine in the subject to undetectable levels for a period of at least 3 days to 10 days.

* * * * *